United States Patent
Takeda et al.

(10) Patent No.: US 9,326,750 B2
(45) Date of Patent: May 3, 2016

(54) ULTRASOUND DIAGNOSTIC IMAGING APPARATUS

(71) Applicants: Yoshihiro Takeda, Hachioji (JP); Daisuke Kaji, Hachioji (JP)

(72) Inventors: Yoshihiro Takeda, Hachioji (JP); Daisuke Kaji, Hachioji (JP)

(73) Assignee: KONICA MINOLTA MEDICAL & GRAPHIC, INC., Tokyo (JP)

(*) Notice: Subject to any disclaimer, the term of this patent is extended or adjusted under 35 U.S.C. 154(b) by 236 days.

(21) Appl. No.: 13/843,654

(22) Filed: Mar. 15, 2013

(65) Prior Publication Data

US 2013/0274608 A1    Oct. 17, 2013

(30) Foreign Application Priority Data

Mar. 16, 2012  (JP) ................. 2012-060594

(51) Int. Cl.
*A61B 8/00*  (2006.01)
*A61B 8/08*  (2006.01)

(52) U.S. Cl.
CPC ............ *A61B 8/0841* (2013.01); *A61B 8/4444* (2013.01); *A61B 8/4405* (2013.01)

(58) Field of Classification Search
CPC ........ A61B 5/0048; A61B 8/08; A61B 8/485; A61B 5/00; A61B 8/00
See application file for complete search history.

(56) References Cited

U.S. PATENT DOCUMENTS

| 8,682,080 B2 | 3/2014 | Soutsuka et al. | |
| 2003/0097066 A1* | 5/2003 | Shelby | A61B 8/0833 600/443 |
| 2005/0256407 A1 | 11/2005 | Hamada | |
| 2006/0106309 A1 | 5/2006 | Liu | |
| 2007/0016035 A1 | 1/2007 | Hashimoto | |
| 2007/0213616 A1* | 9/2007 | Anderson et al. | 600/448 |

(Continued)

FOREIGN PATENT DOCUMENTS

| JP | 2005294932 A | 10/2005 |
| JP | 2005319199 A | 11/2005 |

(Continued)

OTHER PUBLICATIONS

Japanese Office Action (and English translation thereof) dated May 19, 2015, issued in counterpart Japanese Application No. 2012-060594.

*Primary Examiner* — Joel Lamprecht
(74) *Attorney, Agent, or Firm* — Holtz, Holtz & Volek PC

(57) ABSTRACT

Disclosed is an ultrasound diagnostic imaging apparatus including an ultrasound probe which outputs a transmission ultrasound toward a subject and a received signal obtained by receiving a reflected ultrasound from the subject, a transmission unit, a receiving unit and a puncture needle position detection unit which obtains a puncture needle echo information indicating an angle and a position of the puncture needle from the plane-wave received signal, and an ultrasound image is displayed on the basis of the received signal, the transmission unit applies the driving signal to the ultrasound probe so that a plane-wave transmission ultrasound is output from the ultrasound probe, and the receiving unit receives a plane-wave received signal which is obtained in such a way that the plane-wave transmission ultrasound is transmitted from the ultrasound probe, reflected by a puncture needle to be the reflected ultrasound and received by the ultrasound probe.

16 Claims, 24 Drawing Sheets

(56) References Cited

U.S. PATENT DOCUMENTS

| | | | |
|---|---|---|---|
| 2009/0066727 A1* | 3/2009 | Lu | G01S 7/52046 345/643 |
| 2009/0245687 A1* | 10/2009 | Jeon et al. | 382/281 |
| 2010/0204579 A1 | 8/2010 | Yoshida et al. | |
| 2012/0078103 A1* | 3/2012 | Tashiro et al. | 600/443 |

FOREIGN PATENT DOCUMENTS

| | | |
|---|---|---|
| JP | 2006142026 A | 6/2006 |
| JP | 2006-320378 A | 11/2006 |
| JP | 2007000226 A | 1/2007 |
| JP | 2010183935 A | 8/2010 |
| WO | 2010116774 A1 | 10/2010 |

* cited by examiner

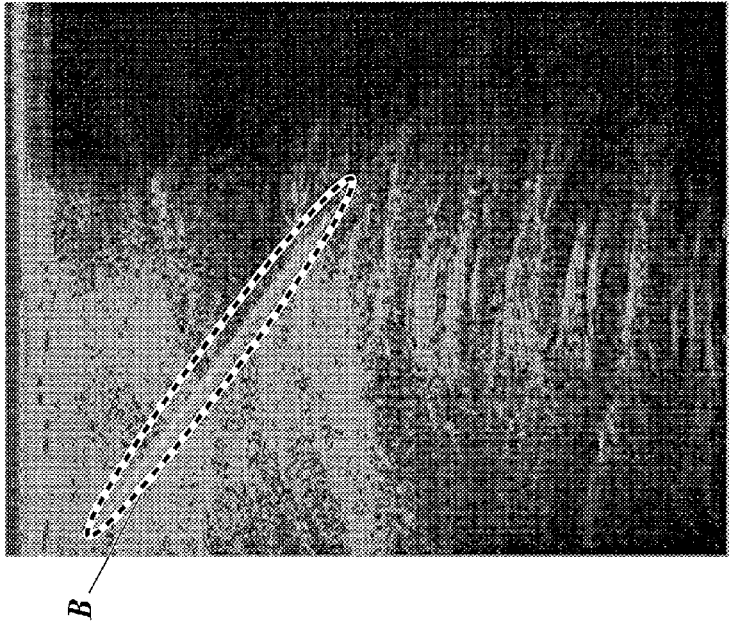
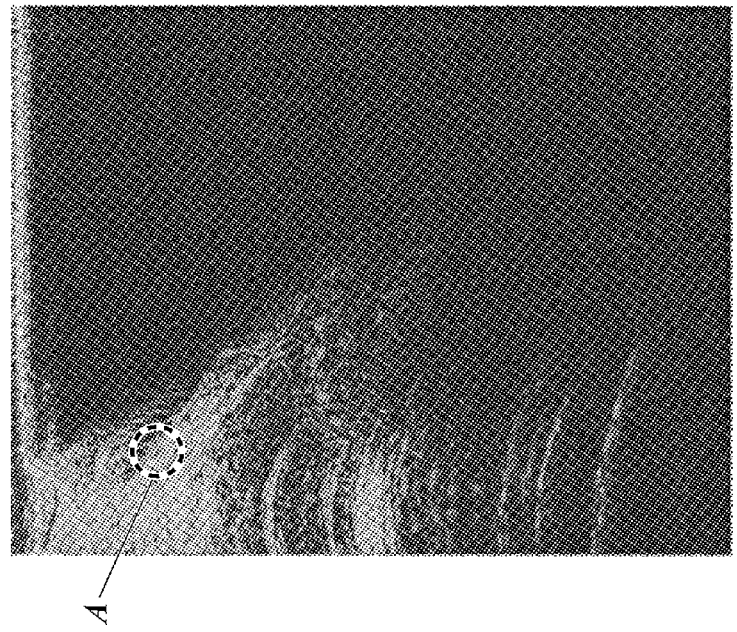

ULTRASOUND DIAGNOSTIC IMAGING APPARATUS

BACKGROUND OF THE INVENTION

1. Field of the Invention

The present invention relates to an ultrasound diagnostic imaging apparatus.

2. Description of Related Art

Biopsy has been long performed where a puncture needle is inserted to a living body to sample a tissue or body fluid which is to be diagnosed. In order not to insert a puncture needle into an incorrect position when sampling a specific tissue or the like of a living body, the puncture needle is attached to an ultrasound probe equipped with an attachment or a guide, as well as an operator such as a doctor checks the position of the puncture by watching an ultrasound image which is based on ultrasound image data on the living body obtained by the ultrasound probe when he or she inserts the puncture needle.

Among ultrasound diagnostic image apparatuses in the earlier development, there is one which distinctly displays a puncture needle in an ultrasound image in such a way that ultrasound is transmitted in multiple directions to detect the direction of the puncture needle on the basis of the strength of received signals, subsequently ultrasound is transmitted and received in the direction perpendicular to the puncture needle so as to obtain a puncture needle image data while ultrasound scanning is performed on an living body so as to obtain a biological tissue image data, and these image data are then composite. Further, JP 2006-320378 discloses an apparatus that transmits and receives ultrasound in the direction perpendicular to a puncture angle which is fixed by a puncture needle insertion attachment.

SUMMARY OF THE INVENTION

However, since the technique disclosed in JP 2006-320378 requires transmitting and receiving ultrasound in multiple directions in order to determine the direction of the puncture needle, there is a problem that the frame rate decreases in exchange for determining the puncture needle. Also, although the technique disclosed in JP 2006-320378 enables to figure out the angle of the puncture needle from the transmitting and receiving directions of the ultrasound and the puncture angle defined by the puncture needle insertion attachment, it cannot determine the depth of the puncture needle. It is thus impossible to figure out the exact position of the puncture needle.

The present invention was made in consideration of the above problems and an object of the present invention is to provide an ultrasonic diagnostic imaging apparatus which can figure out the position of a puncture needle while the decrease in frame rate is reduced.

To realize the above object, an ultrasound diagnostic imaging apparatus reflecting one aspect of the present invention includes an ultrasound probe which is driven by a driving signal to output a transmission ultrasound toward a subject and which outputs a received signal obtained by receiving a reflected ultrasound from the subject, a transmission unit which applies the driving signal to the ultrasound probe, a receiving unit which receives the received signal which is output from the ultrasound probe and a puncture needle position detection unit which obtains a puncture needle echo information indicating an angle and a position of the puncture needle inserted in the subject from the plane-wave received signal received by the receiving unit, and an ultrasound image is displayed on the basis of the received signal received by the receiving unit, the transmission unit applies the driving signal to the ultrasound probe so that a plane-wave transmission ultrasound is output from the ultrasound probe, the receiving unit receives a plane-wave received signal which is obtained in such a way that the plane-wave transmission ultrasound is transmitted from the ultrasound probe, reflected by a puncture needle which is inserted in the subject to be the reflected ultrasound, and received by the ultrasound probe.

Preferably, the puncture needle position detection unit performs a Hough transform on the plane-wave received signal received by the receiving unit, and obtains the puncture needle echo information on the basis of a result of the Hough transform.

Preferably, the puncture needle position detection unit extracts an edge on the basis of change in intensity of the plane-wave received signal received by the receiving unit, and performs the Hough transform on the plane-wave received signal in which the edge is detected.

Preferably, the ultrasound probe comprises a plurality of transducers and outputs the transmission ultrasound from the plurality of transducers, and the puncture needle position detection unit develops the plane-wave received signal of each of the plurality of the transducers received by the receiving unit onto an x-y space where x and y represent a position of each transducer and a depth respectively, performs the Hough transform on the received signal developed on the x-y space, and obtains the puncture needle echo information on the basis of a straight line on the x-y space which is specified by a point having a maximum vote, the vote being the number of sine curves which pass through the point among a plurality of sine curves obtained by the Hough transform.

Preferably, the puncture needle position detection unit detects an edge intensity on the basis of change in intensity of the plane-wave received signal received by the receiving unit, and weights the vote with respect to each of the plurality of the sine curves according to the detected edge intensity.

Preferably, the puncture needle position detection unit obtains puncture access information which specifies the insertion angle and the depth of the puncture needle inserted in the subject on the basis of a distance between the ultrasound probe and a straight line which is determined by the obtained puncture needle echo information.

Preferably, the ultrasound diagnostic imaging apparatus further includes a phasing addition unit which co-phases and adds the received signal obtained from the reflected ultrasound from the subject with reference to a first receiving aperture center and an image generation unit which generates image data for displaying an ultrasound image on the basis of the received signal which is co-phased and added, and the phasing addition unit sets a shift amount of a receiving aperture center on the basis of the puncture access information, and co-phases and adds the received signal with reference to a second receiving aperture center which is shifted by the determined shift amount from the first receiving aperture center, and the image generation unit generates puncture needle image data in which a puncture needle image is enhanced on the basis of the received signal which is co-phased and added by the phasing addition unit with reference to the second receiving aperture center, the puncture needle image being an image of the puncture needle inserted in the subject.

Preferably, the image generation unit composites the puncture needle image data with the image data generated from the received signal which is co-phased and added with reference to the first receiving aperture center.

Preferably, the image generation unit generates the image data by converting intensity of the received signal which is co-phased and added by the phasing addition unit to brightness, and the image generation unit generates image data by log-compressing the received signal which is co-phased and added with reference to the first receiving aperture center, extracts the received signal having a predetermined intensity with respect to the received signal which is co-phased and added with respect the second receiving aperture center, and the intensity of the extracted received signal is converted to brightness so as to generate the puncture needle image data.

Preferably, the image generation unit defines an area which the puncture needle image data is generated from on the basis of the puncture access information, and generates the puncture needle image data of the defined area from the received signal which is co-phased and added with reference to the second receiving aperture center.

Preferably, the ultrasound diagnostic imaging apparatus further includes a sound velocity calculation unit which calculates a sound velocity in the subject on the basis of the puncture needle echo information obtained by the puncture needle position detection unit.

Preferably, the phasing addition unit co-phases and adds the received signal on the basis of the sound velocity calculated by the sound velocity calculation unit.

Preferably, the transmission unit applies the driving signal to the ultrasound probe so that a plane-wave transmission ultrasound is output from an end of the ultrasound probe.

Preferably, the transmission unit applies the driving signal to the ultrasound probe so that the plane-wave transmission ultrasound is output from both ends of the ultrasound probe in an orientation direction.

Preferably, the transmission unit applies the driving signal to the ultrasound probe so that the ultrasound probe outputs the plane-wave transmission ultrasound in a direction outward from the ultrasound probe at a certain angle to a depth direction.

BRIEF DESCRIPTION OF THE DRAWINGS

The present invention will become more fully understood from the detailed description given hereinbelow and the appended drawings which are given byway of illustration only, and thus are not intended as a definition of the limits of the present invention, and wherein:

FIG. 10A is a view for describing a received signal;

FIG. 10B is a view for describing a received signal;

DESCRIPTION OF THE PREFERRED EMBODIMENTS

Figure 1:
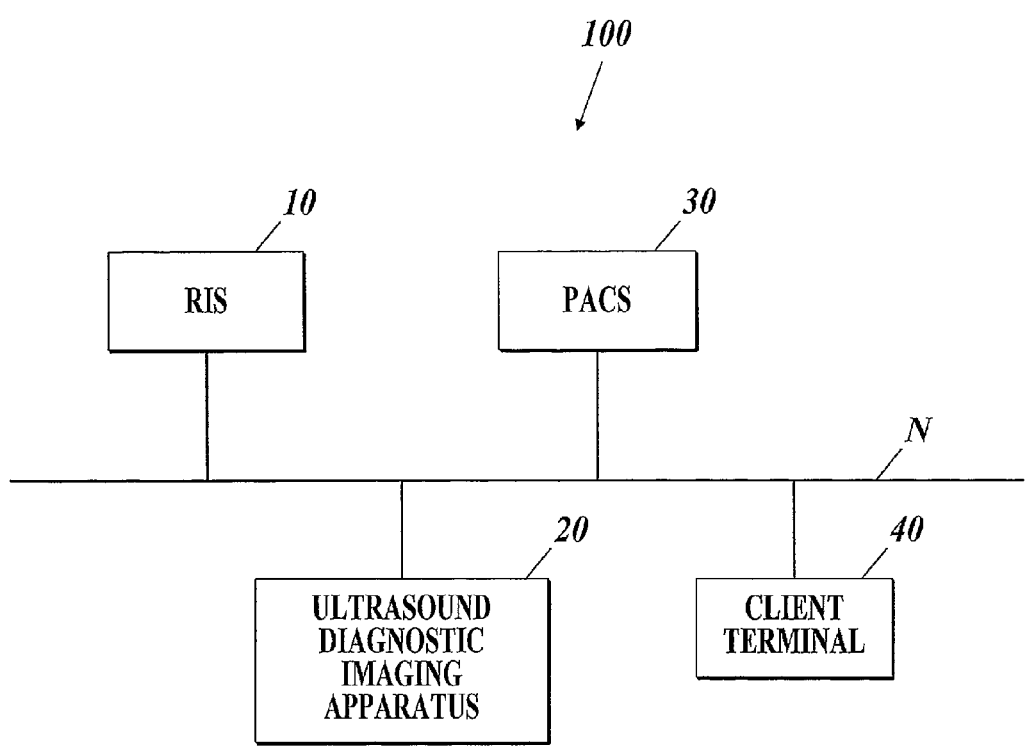
FIG. 1 is a system configuration of a medical image management system according to an embodiment.

Hereinafter, a medical image management system according to embodiments of the present invention will be described with reference to the drawings. However, the scope of the invention is not limited to the examples shown in the drawings. In the following descriptions, same references are used for same functions and configurations and their descriptions are omitted.

As shown in FIG. 1, a medical image management system 100 includes an RIS (radiological information system) 10, an ultrasound diagnostic imaging apparatus 20, a PACS (picture archiving and communication system) 30 and a client terminal 40.

These apparatuses are each connected to one another through a communication network N such as LAN (local area network) so that data communication is possible. The medical image management system 100 may be connected with a different type of modality from the ultrasound diagnostic imaging apparatus 20, for example, such as a CT (computed tomography apparatus), MRI (magnetic resonance imaging apparatus), CR (computed radiography apparatus), DR (digital radiography apparatus), XA (X-ray angiography apparatus) and ES (endoscope).

The RIS 10 manages information within the medical image management system 100 such as appointments for a doctor, reports on diagnosis and past records. The RIS 10 sends image capturing order information, which is generated by an electronic medical record system (not shown) or the like, to the ultrasound diagnostic imaging apparatus 20.

The ultrasound diagnostic imaging apparatus 20 is an apparatus which outputs and displays the condition of a biological inner tissue of a patient (hereinafter also referred to as a subject) as an ultrasound image according to the image capturing order information received from the RIS 10. Specifically, the ultrasound diagnostic imaging apparatus 20 transmits ultrasound (transmission ultrasound) into a subject such as living body, as well as it receives a reflected wave of the ultrasound (reflected ultrasound: echo) which was reflected inside the subject. The ultrasound diagnostic imaging apparatus 20 converts the received reflected ultrasound to an electric signal, and generates ultrasound image data on the basis of the electric signal. The ultrasound diagnostic imaging apparatus 20 displays the inner condition of the subject as an ultrasound image on the basis of the generated ultrasound image data. The ultrasound diagnostic imaging apparatus 20 also generates supplementary information of the generated ultrasound image data on the basis of the image capturing order information. The ultrasound diagnostic imaging apparatus 20 may add the supplementary information to the ultrasound image data to generate an image file of a DICOM (digital imaging and communication in medicine) image data which meets the DICOM standard, and may send it to the PACS 30.

Figure 2:
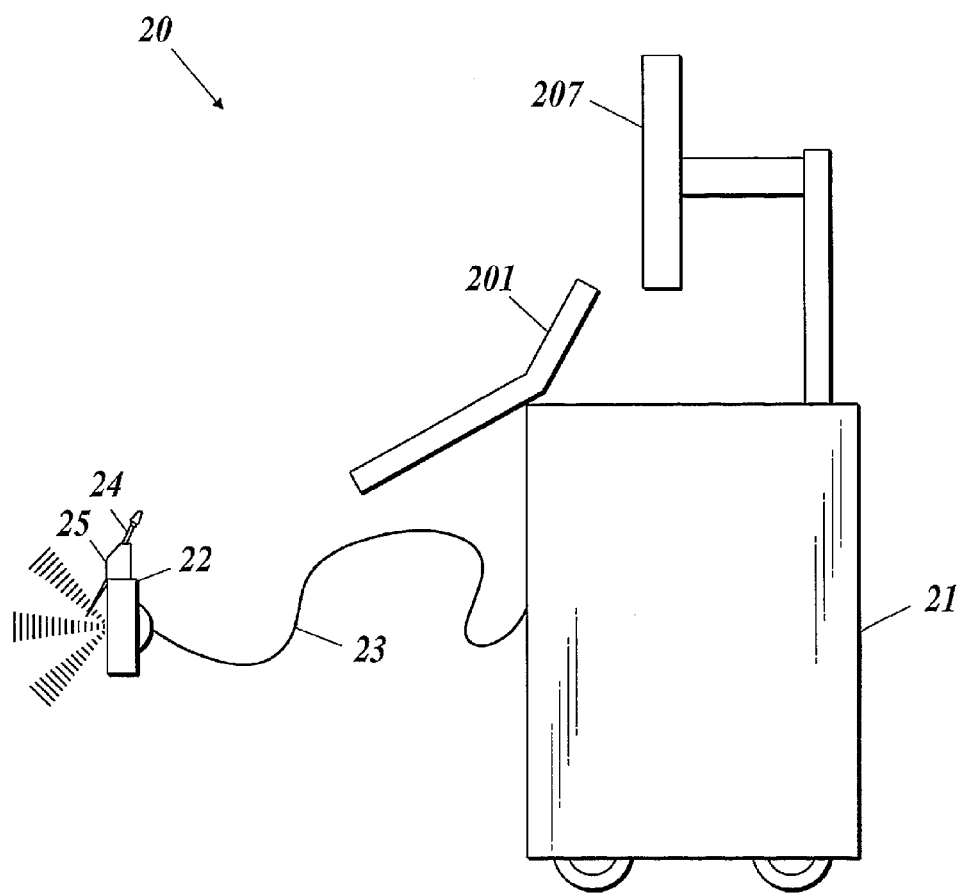
FIG. 2 is a view showing an outer configuration of an ultrasound diagnostic imaging apparatus.

As shown in FIG. 2, the ultrasound diagnostic imaging apparatus 20 includes an ultrasound diagnostic imaging apparatus main body 21 and an ultrasound probe 22. The ultrasound probe 22 transmits the transmission ultrasound as well as receives the reflected ultrasound as described above. The ultrasound diagnostic imaging apparatus main body 21 is connected with the ultrasound probe 22 through a cable 23, and sends an electric driving signal to the ultrasound probe 22 so that the ultrasound probe 22 transmits the transmission ultrasound into the subject. The ultrasound diagnostic imaging apparatus main body 21 receives an electric received signal which is generated at the ultrasound probe 22 according to the reflected ultrasound from the subject received by the ultrasound probe 22, and generates the ultrasound image data as described above.

The ultrasound probe 22 includes a transducer 22a (see FIG. 3) of a piezoelectric element. For example, a plurality of the transducers 22a are arranged in a one-dimensional array in the orientation direction (scanning direction). In the embodiment, the ultrasound probe 22 includes the n (e.g. 192) transducers 22a constituting 1 to n channels. The transducers may also be arranged in a two-dimensional array. The number of the transducers 22a may be appropriately set. The embodiment employs an electronic-scanning linear probe as the ultrasound probe 22. However, any type of electronic-scanning and mechanical-scanning may be employed, and any type of linear scanning, sector scanning and convex scanning may also be employed.

An attachment 25 to guide insertion of the puncture needle 24 in the orientation direction is provided at the side of the ultrasound probe 22. The attachment 25 guides the puncture needle 24 so that the insertion angle thereof is fixed. The insertion angle is adjustable.

Instead of providing the attachment 25, for example, a guide groove to guide the insertion angle of the puncture needle 24 may be provided to the ultrasound probe 22 in the embodiment.

Figure 3:
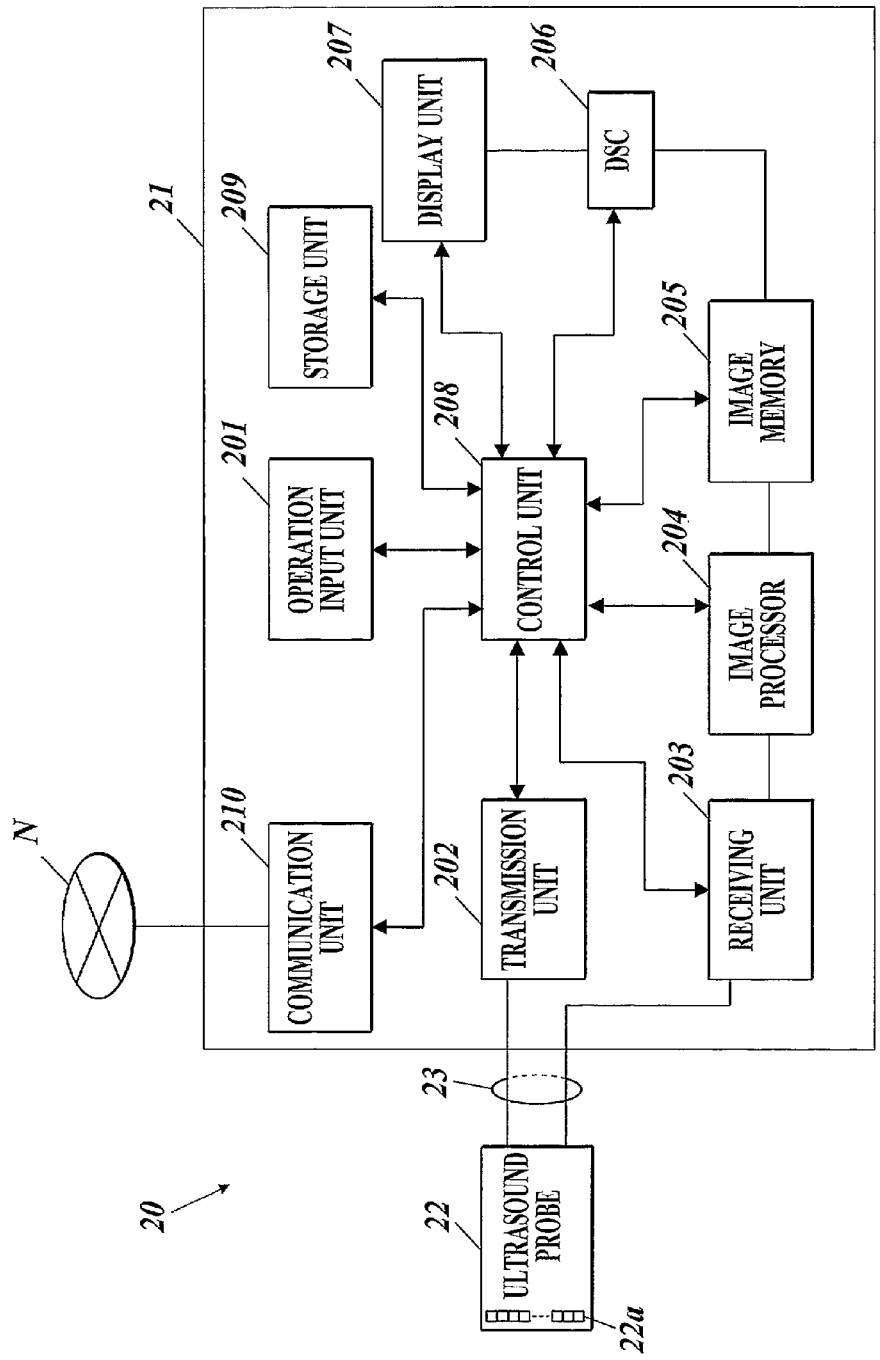
FIG. 3 is a block diagram showing a schematic configuration of the ultrasound diagnostic imaging apparatus.

As shown in FIG. 3, the ultrasound diagnostic imaging apparatus main body 21 includes, for example, an operation input unit 201, a transmission unit 202, a receiving unit 203, an image processor 204, an image memory 205, a DSC (digital scan converter) 206, a display unit 207, control unit 208, a storage unit 209 and a communication unit 210.

The operation input unit 201 includes, for example, switches, buttons, a trackball, a mouse, a keyboard and the like for inputting a command of starting diagnosis, data such as personal information of a subject and various parameters for displaying the ultrasound image on the display unit 207. The operation input unit 201 outputs an operation signal to the control unit 208.

The transmission unit 202 supplies the electric driving signal to the ultrasound probe 22 through the cable 23 by being controlled by the control unit 208 so that the ultrasound probe 22 generates the transmission ultrasound. Specifically, the transmission unit 202 includes, for example, a clock generator circuit, a delay circuit and a pulse generator circuit. The clock generator circuit generates a clock signal which determines the transmission timing and the transmission frequency of the driving signal. The delay circuit sets delay time of the transmission timing of the driving signal with respect to each of the dedicated paths which correspond to respective transducers, and delays the transmission of the driving signal by the set delay time so as to focus the ultrasound beam consisting of the transmission ultrasound (transmission beam forming). The pulse generator circuit generates a pulse signal as the driving signal with a predetermined period. The transmission unit 202 as configured above drives, for example, a certain contiguous part (e.g. 64 pieces) of the n (e.g. 192) transducers arrayed in the ultrasound probe 22, so as to generate the transmission ultrasound. Such ultrasound beam to be focused may be called scanning beam. The transmission unit 202 shifts the driving transducers in the orientation direction each time the transmission ultrasound is generated, and thus performs a scan. In the embodiment, when the transmission unit 202 does not delay the driving signal by the delay circuit, it also applies such a driving signal to the ultrasound probe 22 that the plurality of transducers drives simultaneously. The ultrasound probe 22 can thus generate an ultrasound beam of a plane wave having a certain beam width. The ultrasound beam as generated above may be called a puncture needle searching beam, and is used for searching the puncture needle as described below. The transmission unit 202 can also generate a sound velocity analyzing beam where the ultrasound beam is focused as described below.

Figure 4:
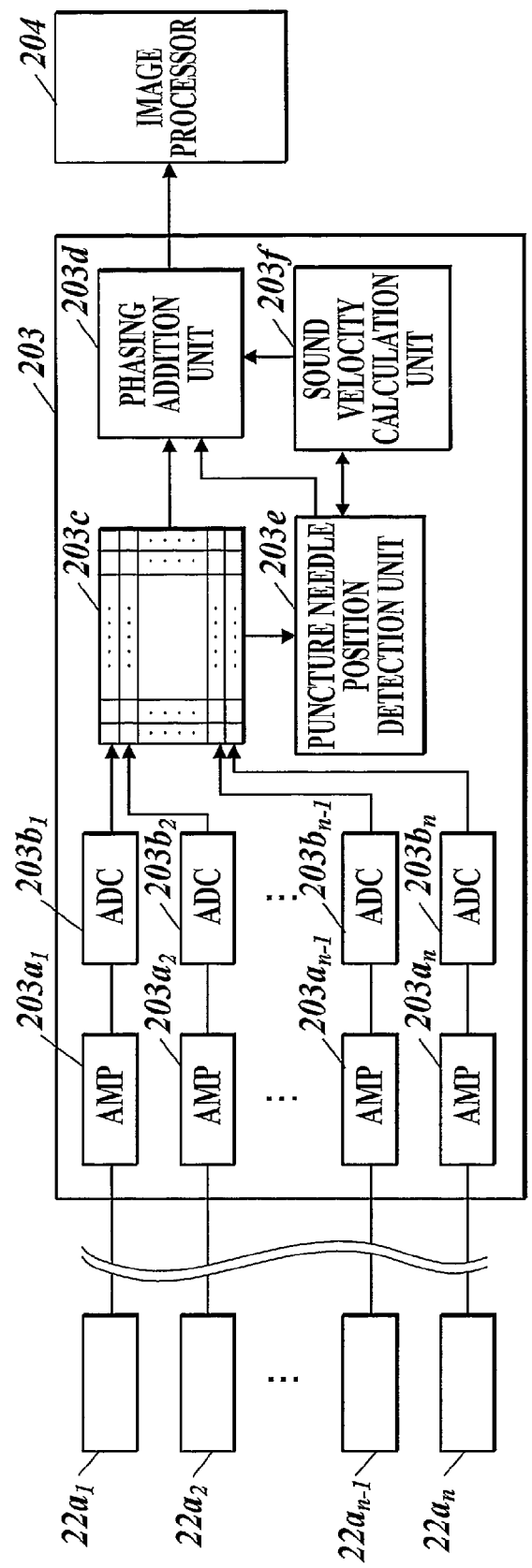
FIG. 4 is a block diagram showing a functional configuration of a receiving unit.

The receiving unit 203 is a circuit which receives electric received signals from the ultrasound probe 22 through the cable 23 by being controlled by the control unit 208. As shown in FIG. 4, the receiving unit 203 includes, for example, an AMP (amplifier) 203a, an ADC (analog-digital converter) 203b, a sampling memory 203c, a phasing addition unit 203d, a puncture needle position detection unit 203e and a sound velocity calculation unit 203f.

The AMP 203a is a circuit which amplifies the received signals at a preset amplification factor on each of the dedicated paths corresponding to respective n transducers $22a_1$ to $22a_n$. In the embodiment, the n AMPs $203a_1$ to $203a_n$ are provided corresponding to the respective n transducers $22a_1$ to $22a_n$.

The ADC 203b is a circuit which performs analog-to-digital conversion (A/D conversion) to the received signals amplified by the AMPs 203a for sampling the signals. In the embodiment, the n ADCs $203b_1$ to $203b_n$ are provided corresponding to the respective n AMPs $203a_1$ to $203a_n$.

The sampling memory 203c has a memory area of multiple channels corresponding to the respective transducers $22a_1$ to $22a_n$, and each channel has a plurality of sampling storage areas. The sampling memory 203c shifts the A/D converted received signals which are stored in the plurality of sampling storage areas with every sampling of the received signals, for example, in the manner of FIFO (first-in/first-out). The sampling memory 203c thus stores the received signals in chronological order.

The phasing addition unit 203d reads the received signals stored in the sampling memory 203c in such a manner that reading areas of respective channels are shifted according to the delay time with reference to the received signal of the channel which corresponds to a predetermined receiving aperture center. The phasing addition unit 203d then adds these data. Specifically, the phasing addition unit 203d adds the delay time to the respective A/D converted received signals so as to align the time phase, and then add them (phasing addition) to generate sound ray data. In other words, the phasing addition unit 203d performs received beam forming in the manner as described above to generate the sound ray data. The delay time is based on a set sound velocity. The phasing addition unit 203d outputs the generated sound ray data to the image processor 204.

When the sampling memory 203c stores the received signals which are obtained from the reflected ultrasound of the puncture needle searching beam as transmitted above, the puncture needle position detection unit 203e analyzes these received signals to generate puncture needle echo information which indicates the angle and position of the puncture needle 24 inserted in the subject. Based on the generated puncture needle echo information, the puncture needle position detection unit 203e also generates puncture access information which specifies the actual insert angle and depth of the puncture needle 24 inserted in the subject. Specific methods of generating the puncture needle echo information and puncture access information are described below. Based on the generated puncture access information, the puncture needle position detection unit 203e then tells the phasing addition unit 203d the channel which corresponds to the receiving aperture center in the phasing addition in order that it generates the sound ray data which includes the puncture needle image data described below.

When the sampling memory 203c stores the received signals which are obtained by sending and receiving the sound velocity analyzing beam, the sound velocity calculation unit 203f corrects the puncture needle echo information as well as calculates the sound velocity in the subject on the basis of the puncture needle echo information which is generated at the puncture needle position detection unit 203e. Specific methods of correcting the puncture needle echo information and calculating the sound velocity are described below. The sound velocity calculation unit 203f then tells the phasing addition unit 203d the delay time based on the calculated sound velocity.

The image processor 204 carries out brightness conversion on the sound ray data from the receiving unit 203 by performing envelope detection, logarithmic compression and the like on the data, and further adjusting the dynamic range and gain. The image processor 204 thus generates B-mode image data. That is, the B-mode image data represents the intensity of the received signals by brightness. Besides the B-mode image data, the image processor 204 may be able to generate A-mode image data, M-mode image data or image data of Doppler sonography.

Figure 5:
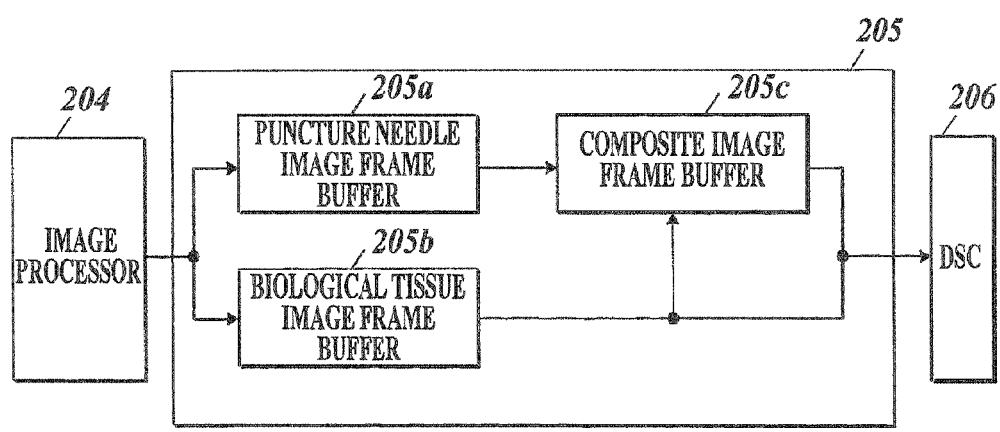
FIG. 5 is a block diagram showing a functional configuration of an image memory.

The image memory 205 is made of, for example, a semiconductor memory such as DRAM (dynamic random access memory), and stores the B-mode image data sent from the image processor 204 on a frame basis. A frame of the B-mode image data may be called an ultrasound image data or a frame image data. The image memory 205 is made of a high-capacity memory which is capable of holding the frame image data of a predetermined time period (for example, 5 min), and holds the ultrasound image data of the latest predetermined time period in a FIFO manner. Specifically, the image memory 205 includes, as shown in FIG. 5, for example, a puncture needle image frame buffer 205a, a biological tissue image frame buffer 205b and a composite image frame buffer 205c.

The puncture needle image frame buffer 205a stores the puncture image data on a frame basis. The biological tissue image frame buffer 205b stores biological tissue image data on the biological tissue in the subject on a frame basis. Specifically, it stores the ultrasound image data which is obtained by co-phasing and adding the received signals in such a manner that the receiving aperture center is set at the channel which corresponds to the transmission aperture center of the transmitted ultrasound beam. The composite image frame buffer 205c stores a composite image data on a frame basis, which is a composite ultrasound image data of the puncture needle image data and biological tissue image data which are respectively read out from the puncture needle image frame buffer 205a and biological tissue image frame buffer 205b.

The ultrasound image data as generated above is sent from the image memory 205 to the DSC 206 by one frame every predetermined time by being controlled by the control unit 208.

The DSC 206 converts the ultrasound image data received from the image memory 205 to an image signal in scanning format of the television signal, and outputs it to the display unit 207.

The display unit 207 can be a display device such as LCD (liquid crystal display), CRT (cathode-ray tube) display, organic EL (electronic luminescence) display, inorganic EL display and plasma display. The display unit 207 displays the ultrasound image on a display screen according to the image signal output from the DSC 206. The embodiment employs a 15-inch LCD with a white or full-color LED (light-emitting diode) backlight as the display unit 207. The LCD with a white backlight may have a function of adjusting the brightness of the LED, for example, by analyzing the ultrasound image data. In this case, the screen may be divided into a plurality of areas and the brightness of the LED may be adjusted in each of the areas. Alternatively, the brightness of the LED may be adjusted over the whole screen. Any screen size is applicable for the display unit 207. The backlight of the display unit 207 is not limited to the LED, and may be, for example, a CCFL (cold cathode fluorescent lamp) or the like.

The control unit 208 includes, for example, a CPU (central processing unit), a ROM (read only memory) and a RAM (random access memory). The control unit 208 reads out various programs stored in the ROM such as system program, develops them on the RAM, and integrally controls the operations of the ultrasound diagnostic imaging apparatus 20 according to the developed programs.

The ROM is made of a semiconductor non-volatile memory or the like, and stores a system program compatible with the ultrasound diagnostic imaging apparatus 20, various data, various processing programs which are executable on the system program, for example, ones for frame image data generating processing or puncture image extraction processing described below, and the like. These programs are stored in the form of program codes which are readable by a computer, and the CPU executes operations according to the program codes one after another.

The storage unit 209 is made of, for example, a high-capacity record medium such as HDD (hard disk drive) and SSD (solid state drive), and is capable of storing the ultrasound image data as generated above. The storage unit 209 is capable of storing a frame of the ultrasound image data on a one-frame still image as well as a video data in which the ultrasound image data on several frames are displayed as a video. Besides the above record medium, a portable record medium such as DVD-R (digital versatile disk-recordable) and CD-R (compact disk-recordable) and a data reading/writing device such as DVD-R drive or CD-R drive for recording data thereon may be provided to the storage unit 209. The storage unit 209 may be capable of storing an image file of the DICOM image data as generated above.

The communication unit 210 includes a LAN adapter, a router, a TA (terminal adapter) and the like, and sends and receives data to and from external devices such as the RIS 10, PACS 30 and client terminal 40.

As shown in FIG. 1, the PACS 30 is a database system which keeps the image file and the like generated in the ultrasound diagnostic imaging apparatus 20 and performs search and data analysis. The PACS 30 accumulates the image file received from the ultrasound diagnostic imaging apparatus 20, for example, to a relational database based on the supplementary information included in the image file. The PACS 30 searches the image file based on a search key such as patient ID and examination ID which is designated according to the operation of a diagnostician, and outputs it to an image viewer or imager. When the PACS 30 receives an image file data query including a search key such as patient ID and examination ID from an external device, it can search the image file which matches the query and send it to the external device.

Next, frame image data generation processing will be described with reference to FIG. 6, which is executed at the control unit 208 of the ultrasound diagnostic imaging apparatus 20 in the medical image management system 100 as configured above. The frame image data generation processing is executed when the ultrasound diagnostic imaging apparatus 20 generates ultrasound image data for one frame.

First, the control unit 208 executes a puncture needle recognition processing which puts the puncture needle position detection unit 203*e* into operation, and thus obtains the puncture needle echo information (step S101). The puncture needle recognition processing will be described with reference to FIG. 7.

The control unit 208 sends and receives the puncture needle searching beam as described above (step S201).

The puncture needle 24 has the property of specularly reflecting ultrasound strongly in the subject since it has a sound impedance greatly different from that of the biological tissue in the subject. By means of this property, a plane-wave ultrasound beam is transmitted as the puncture needle searching beam in the embodiment. The plane-wave ultrasound beam which is transmitted for searching the puncture needle is also called "the puncture needle searching transmission ultrasound". Specifically, if the transmitted ultrasound beam is focused, the received signals obtained from the ultrasound reflected on the puncture needle 24 show up as seen in the area A surrounded by the dotted line in FIG. 10A. Thus, there is no specific received signals, and the puncture needle 24 is difficult to detect. On the contrary, if the transmitted ultrasound beam is a plane wave, the ultrasound reflected on the puncture needle 24 forms a plane wave. The receives signals obtained from the reflected ultrasound beams on the puncture needle 24 show up as seen in the area B surrounded by the dotted line in FIG. 10B. As a result, the rectilinear received signals are obtained, and the puncture needle 24 can be detected with such signals. As described above, the puncture needle 24 is detected by sending and receiving the puncture needle searching beam of a plane-wave ultrasound beam just one time in the embodiment. The decrease in frame rate is therefore can be reduced.

Figure 11:
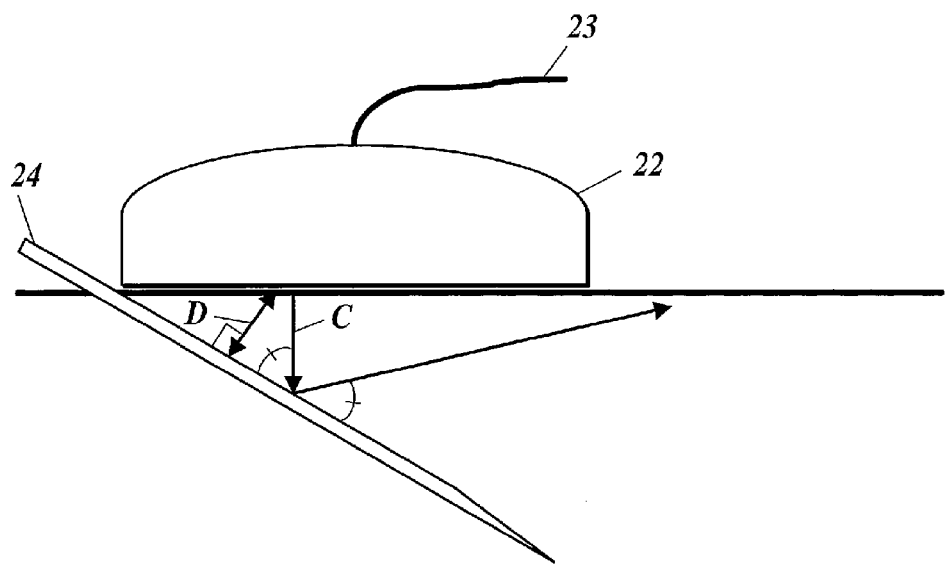
FIG. 11 is a view for describing transmission and reception of a puncture needle searching beam.
Figure 12A:
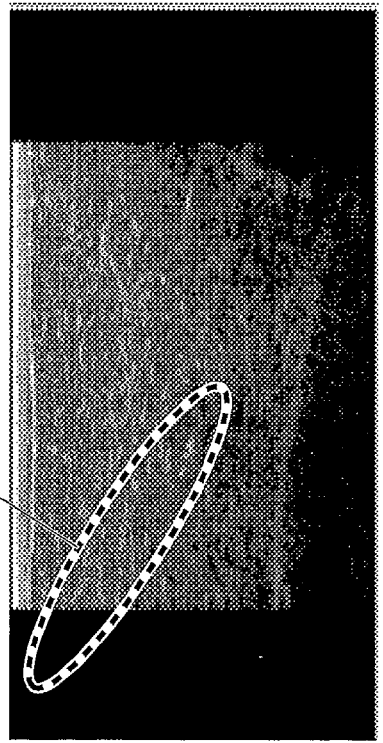
FIG. 12A is a view for describing a received signal obtained from reflected ultrasound on the puncture needle.
Figure 12B:
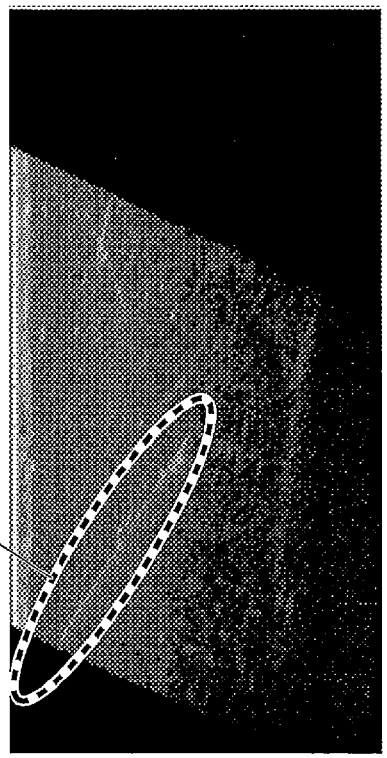
FIG. 12B is a view for describing a received signal obtained from reflected ultrasound on the puncture needle.

The puncture needle searching beam may be transmitted from any part of the ultrasound probe 22. If it is transmitted from an end of the ultrasound probe 22, the puncture needle 24 is recognized rapidly. If the puncture needle searching beams are transmitted from both side ends of the ultrasound probe 22, the puncture needle 24 is recognized rapidly regardless of which side it is inserted from. When the ultrasound probe has two-dimensionally arrayed transducers, it is preferable to transmit the puncture needle searching beams from the four edges. The puncture needle searching beam may be sent in any direction as long as the received signals are obtained from the reflected ultrasound from the puncture needle 24. It is however preferable that it is transmitted in the direction outward from the ultrasound probe at a predetermined angle to the depth direction. It is particularly preferable the direction is perpendicular or approximately perpendicular to the insertion angle of the puncture needle 24 since the accuracy of detecting the puncture needle 24 can be improved. In the case shown in FIG. 11 for example, if the puncture needle searching beam is transmitted in the direction of arrow C, the reflected ultrasound may go beyond a detectable area of the ultrasound probe 22 depending on the insertion angle of the puncture needle 24 since the puncture needle 24 specularly reflects the puncture needle searching beam. In such case, the ultrasound probe 22 does not receive the reflected ultrasound from the puncture needle 24. The received signals of the reflected ultrasound from the puncture needle 24 is thus not clear as seen in the area E surrounded by the dotted line in FIG. 12A. On the contrary, if the puncture needle searching beam is transmitted in the direction perpendicular to the insertion angle of the puncture needle 24 as shown by arrow D in FIG. 11, the ultrasound reflects on the puncture needle 24 into the direction opposite to the transmitted direction. The ultrasound probe 22 can thus receive the reflected ultrasound from the puncture needle 24 in great amount, and the received signals obtained from the reflected ultrasound beam on the puncture needle 24 shows up clearly as seen in the area F surrounded by the dotted line in FIG. 12B. The puncture needle 24 can be therefore easily detected. The received signals obtained from the reflected ultrasound, which is the puncture needle searching transmission ultrasound reflected off the subject, being received and output by the ultrasound probe are also called "the puncture needle searching received signals".

Figure 7:
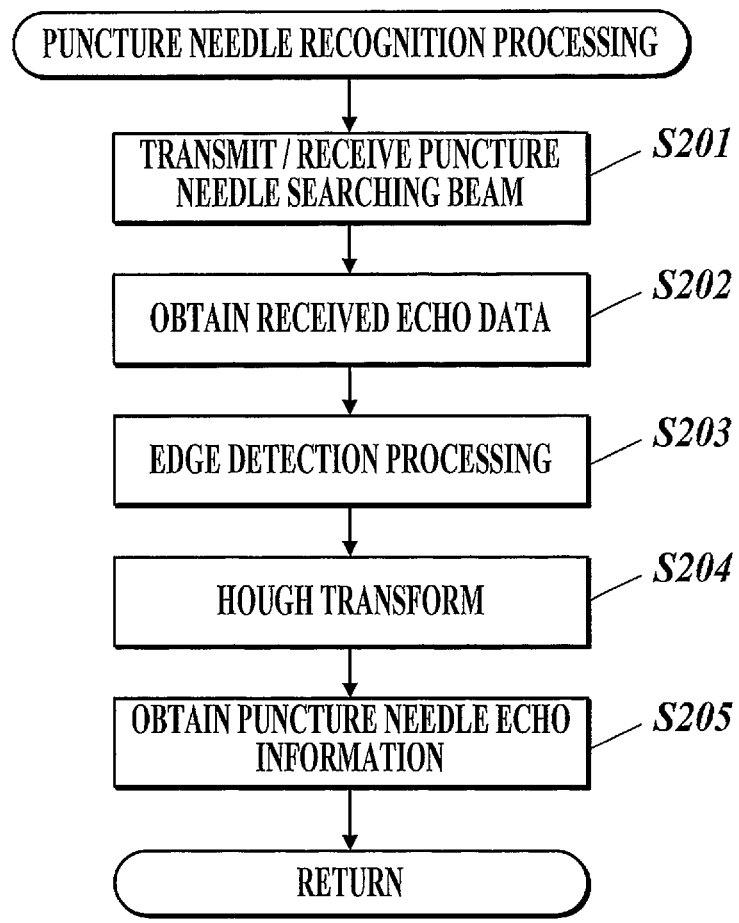
FIG. 7 is a flowchart for describing a puncture needle recognition process.

Subsequently, as shown in FIG. 7, when the sampling memory 203*c* stores the received signals which are obtained from the puncture needle searching beams as received above so that a receive echo data is stored, i.e. the receive echo data of the puncture needle searching beams is obtained (step S202), the control unit 208 executes an edge detection processing (step S203).

In the edge detection processing, the control unit 208 extracts a part where the intensity of the received signals changes by a predetermined level or more. Specifically, the control unit 208 applies, for example, a differential filter, edge enhancing filter or the like to each sampling storage area of the sampling memory 203*c*. The control unit 208 then extracts an edge which is a part where the received signals of adjacent sampling storage areas are different in intensity by the predetermined level or more. Thus, the received signals of the puncture needle searching beam reflected from the puncture needle 24 can be enhanced.

Next, the control unit 208 performs the Hough transform on the edge-detected received echo data (step S204). This gives a parameter (straight line parameter) of a rectilinear part which is formed by the received signals of the puncture needle searching beams reflected from the puncture needle 24.

Figure 13B:
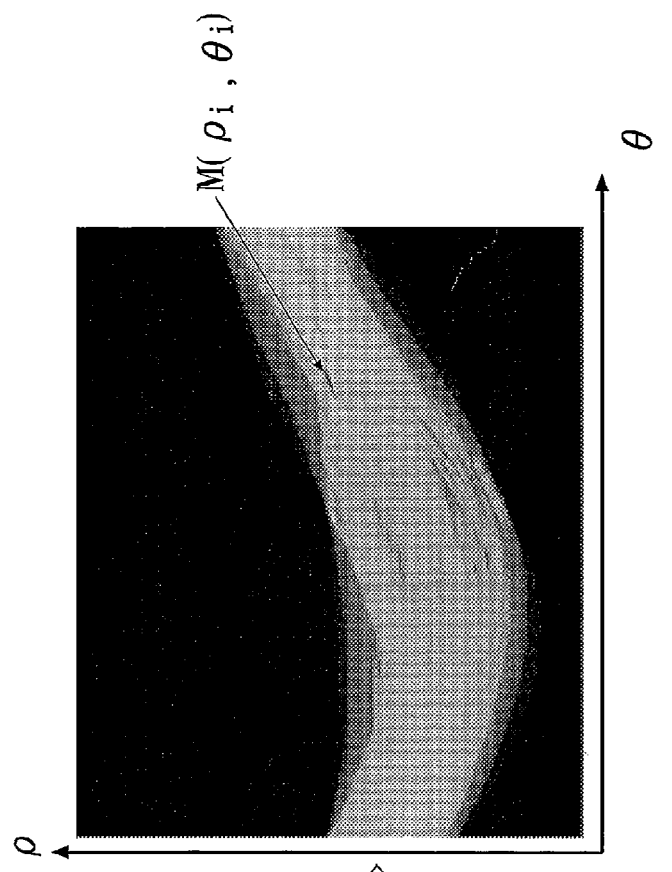
FIGS. 13A and 13B are views for describing the Hough transform.
Figure 13A:
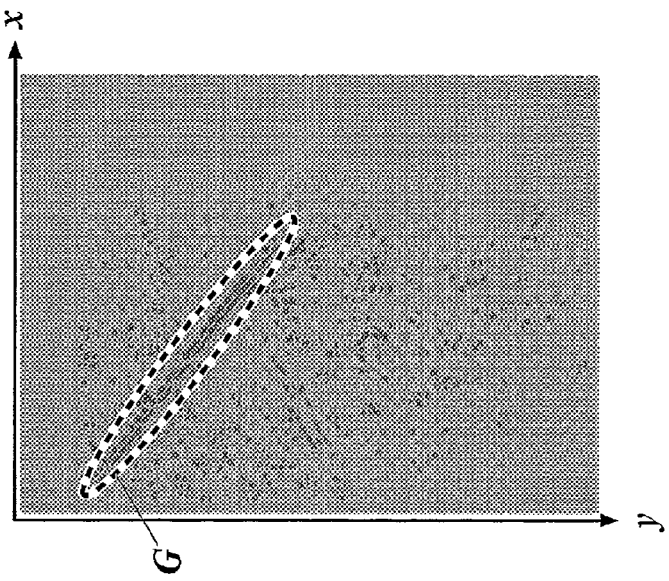

For example, the control unit 208 firstly plots the edge-detected received echo data on an x-y space as show in FIG. 13A, where x represents distance in the orientation direction and y represents depth. The received signals of the puncture needle searching beam are enhanced as seen in the area G surrounded by the dotted line in FIG. 13A. The control unit 208 subsequently performs the Hough transform on the received echo data plotted on the x-y space. Specifically, the control unit 208 transforms each point on the received echo data where the received signals appear into a sine curve on a ρ-θ space. The transform formula is represented by the following formula (1) where $(x_0, y_0)$ represents the coordinate of a certain point on the x-y space.

$$\rho = x_0 \cdot \cos\theta + y_0 \cdot \sin\theta \quad (0 \leq \theta < \pi) \tag{1}$$

The control unit 208 then counts votes for each point which transformed sine curves pass through, and plots the result on the ρ-θ space. For example, FIG. 13B shows the result of the Hough transform on the received echo data of FIG. 13A where votes of the obtained sine curves are plotted.

It is easier to obtain the linear parameter when the votes of each sine curve are weighted according to the edge intensity of the edge-detected received echo data.

Next, the control unit 208 extracts the point which gets the largest number of votes, i.e. the point with the maximum votes, and determines it as the linear parameter. For example, the point M $(\rho_i, \theta_i)$ is the point with the maximum votes in FIG. 13B. This point with the maximum votes represents the linear parameter. If the maximum votes is less than a predetermined threshold, it is determined that the puncture needle 24 is not inserted and the maximum votes is not extracted.

As shown in FIG. 7, the control unit 208 subsequently determines the puncture needle echo information from the linear parameter $(\rho_i, \theta_i)$ (step S205), and then ends the processing. The puncture needle echo information (z) is determined by the following formula (2).

$$z = \tan\theta_i \cdot x + \rho_i / \cos\theta_i \tag{2}$$

The embodiment employs the Hough transform for obtaining the puncture needle echo information. As a result, even if the received signals which have rectilinear property are interrupted in the middle in the receive echo data, for example, the puncture needle echo information can be obtained as described above.

Figure 6:
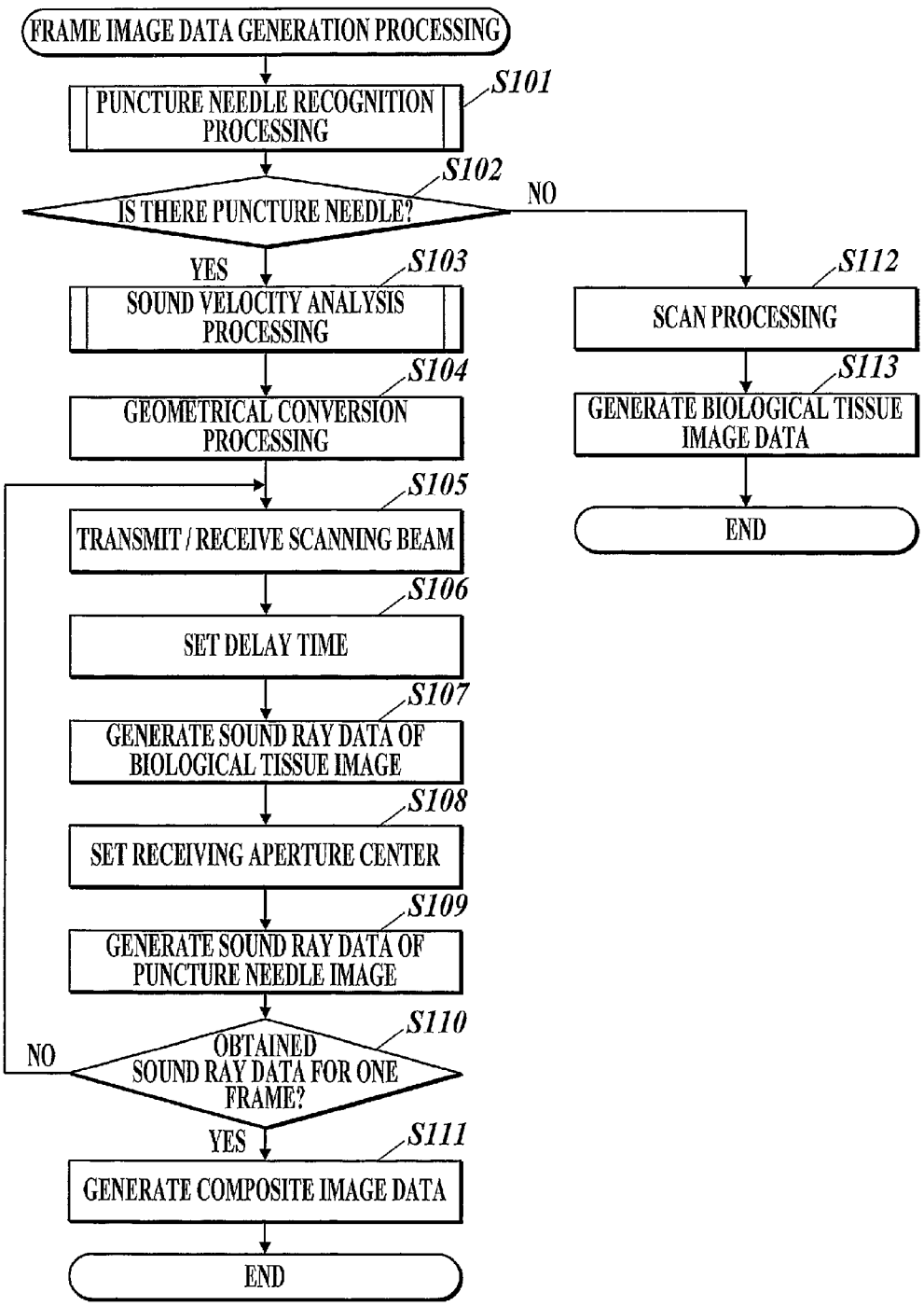
FIG. 6 is a flowchart for describing a flame image data generating process.
Figure 8:
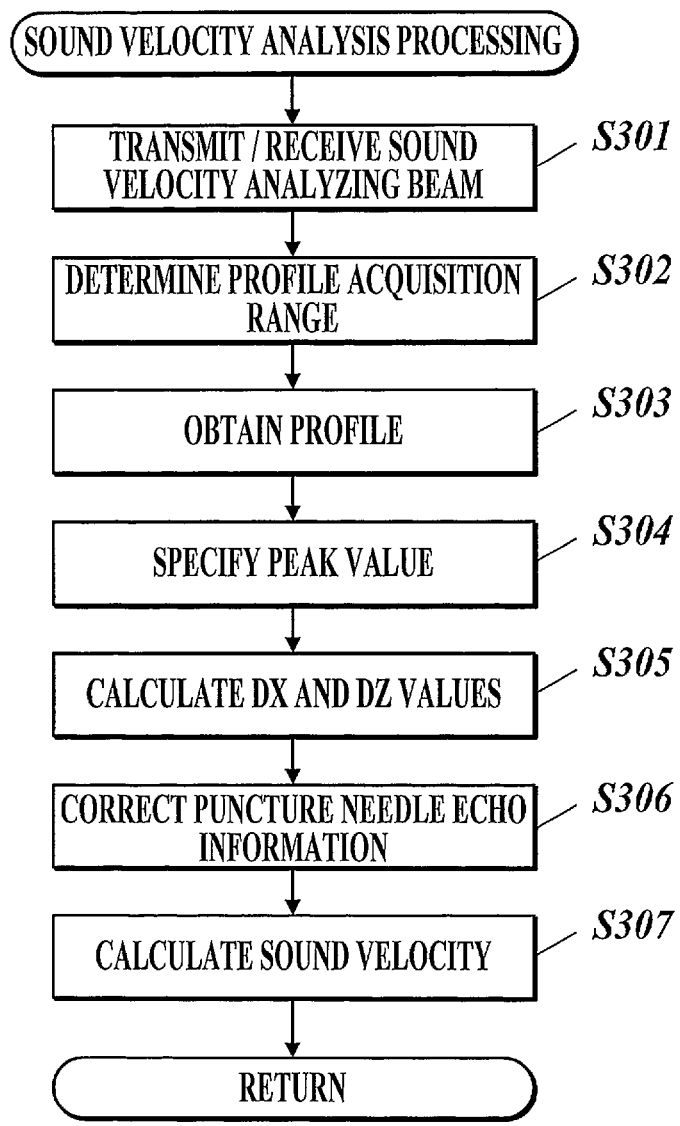
FIG. 8 is a flowchart for describing a sound velocity analyzing process.

As shown in FIG. 6, the control unit 208 subsequently executes the puncture needle recognition processing so as to determine whether the puncture needle 24 is inserted in the subject or not (step S102). Specifically, the puncture needle recognition processing is to determine the presence or absence of the puncture needle 24 based on whether the puncture needle echo information is obtained or not. If the control unit 208 determines there is the puncture needle 24 in the subject (step S102, Y), it executes an sound velocity analysis processing so as to obtain corrected puncture needle echo information and the sound velocity in the subject (step S103). The sound velocity analysis processing will be described in detail with reference to FIG. 8.

The control unit 208 firstly sends and receives the sound velocity analyzing beams as described above (step S301). The sound velocity analyzing beams are, for example, a focused ultrasound beam which is transmitted from 16 channels of the transducers 22a. The number of the transducers 22a which are driven to transmit the sound velocity analyzing beam may be set appropriately.

Next, when the sampling memory 203c stores the receives signals obtained from the received sound velocity analyzing beams and the received echo data is thus obtained, the control unit 208 determines that the received signals in a certain area of the received echo data belong to a profile acquisition area (step S302). That is, the control unit 208 extracts the received signals which is included in a predetermined area around the straight line defined by the puncture needle echo information obtained in the above puncture needle recognition processing, and defines that they belong to the profile acquisition area. Specifically, the control unit 208 defines, for example, a profile acquisition range J as shown in FIG. 14A, which is an area having a predetermined width around the straight line H defined by the puncture needle echo information (z).

The control unit 208 subsequently obtains a profile from the received signals in the defined profile acquisition range (step S303). Specifically, the control unit 208 extracts the maximum intensity of the received signals in the defined profile acquisition range with respect to each channel of the transducers 22a, which is, for example, as represented by reference K in FIG. 14B. In order to smooth noises, a LPF (low-pass filter) may be applied to the extraction result so as to obtain such a result as represented by reference L in FIG. 14B.

The control unit 208 specifies the channel of the transducer 22a which shows the peak value from the profile acquired as described above (step S304). In the example shown in FIG. 14B, the transducer 22a at channel 102 has a received signal intensity of the peak value.

Figure 14C:
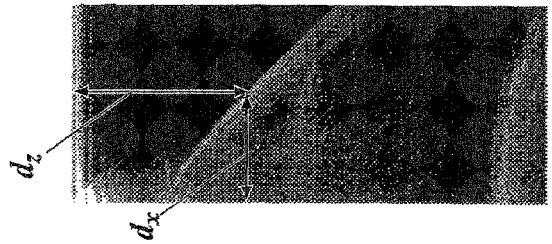
FIGS. 14A, 14B, and 14C are views for describing a process of the sound velocity analysis.

The control unit 208 calculates the values dx and dz shown in FIG. 14C on the basis of the peak value as specified above (step S305).

Figure 14B:
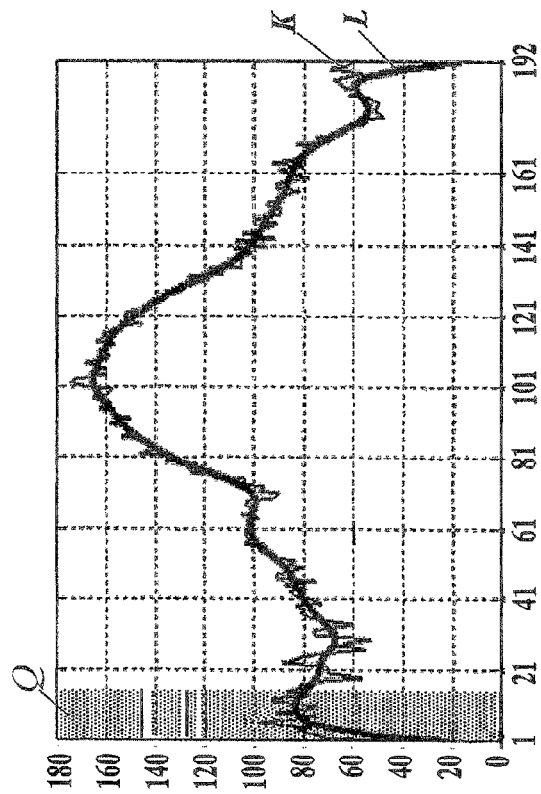
Figure 14A:
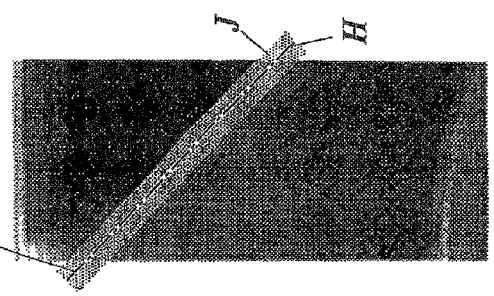

The value of dx represents the distance between the position of the peak received signal and the transmission aperture center of the sound velocity analyzing beam. That is, the value of dx is calculated by specifying the channels of the transducers 22a which respectively corresponds to the peak and the transmission aperture center of the sound velocity analyzing beam. For example, if 16 channels (transmission opening channels) of the transducers 22a which are used to transmit ultrasound of the sound velocity analyzing beam are channels 1 to 16 as shown in FIG. 14B (see reference "Q" in FIG. 14B), the transducers which correspond to the transmission aperture center are at channels 8 and 9. Meanwhile, the transducer 22a which corresponds to the peak is at channel 102. Given the transducers 22a have a pitch of 0.2 mm for example, the value of dx becomes 0.2×(102−8.5)=18.7 mm.

The value of dz represents the distance from the position of the peak received signal to the ultrasound probe 22, or received timing. The value of dz is determined from the above-described puncture needle echo information.

The control unit 208 corrects the puncture needle echo information on the basis of the dx and dz values as calculated above (step S306). Specifically, the control unit 208 firstly corrects the $\theta_i$ value of the linear parameter based on the dx and dz values. The corrected value $\theta_i'$ of $\theta_i$ is determined by the following formula (3).

$$\theta_i' = \tan^{-1}(dx/dz) \tag{3}$$

The control unit 208 also determines the corrected value (z') of the puncture needle echo information (z) with the following formula (4).

$$Z' = z \cdot (dx/dz) \tag{4}$$

The control unit 208 makes the sound velocity calculation unit 203$f$ calculate the corrected sound velocity in the subject on the basis of the $\theta_i'$ value as calculated above (step S307), and then ends the processing. The sound velocity is used to set the delay time for the phasing addition, and the default value thereof is 1540 m/s. The corrected sound velocity (c) is determined by the following formula (5).

$$c = 1540 \times \tan\theta_i' / \tan\theta_i \quad (5)$$

By obtaining the corrected sound velocity, the embodiment is successful in performing the phasing addition correctly and thus obtaining a high-quality ultrasound image.

As shown in FIG. 6, the control unit 208 subsequently executes a geometric transform processing so as to obtain the above-described puncture access information from the puncture needle echo information (step S104).

The puncture access information is determined based on the puncture needle echo information and the law of ultrasound reflection.

Figure 15:
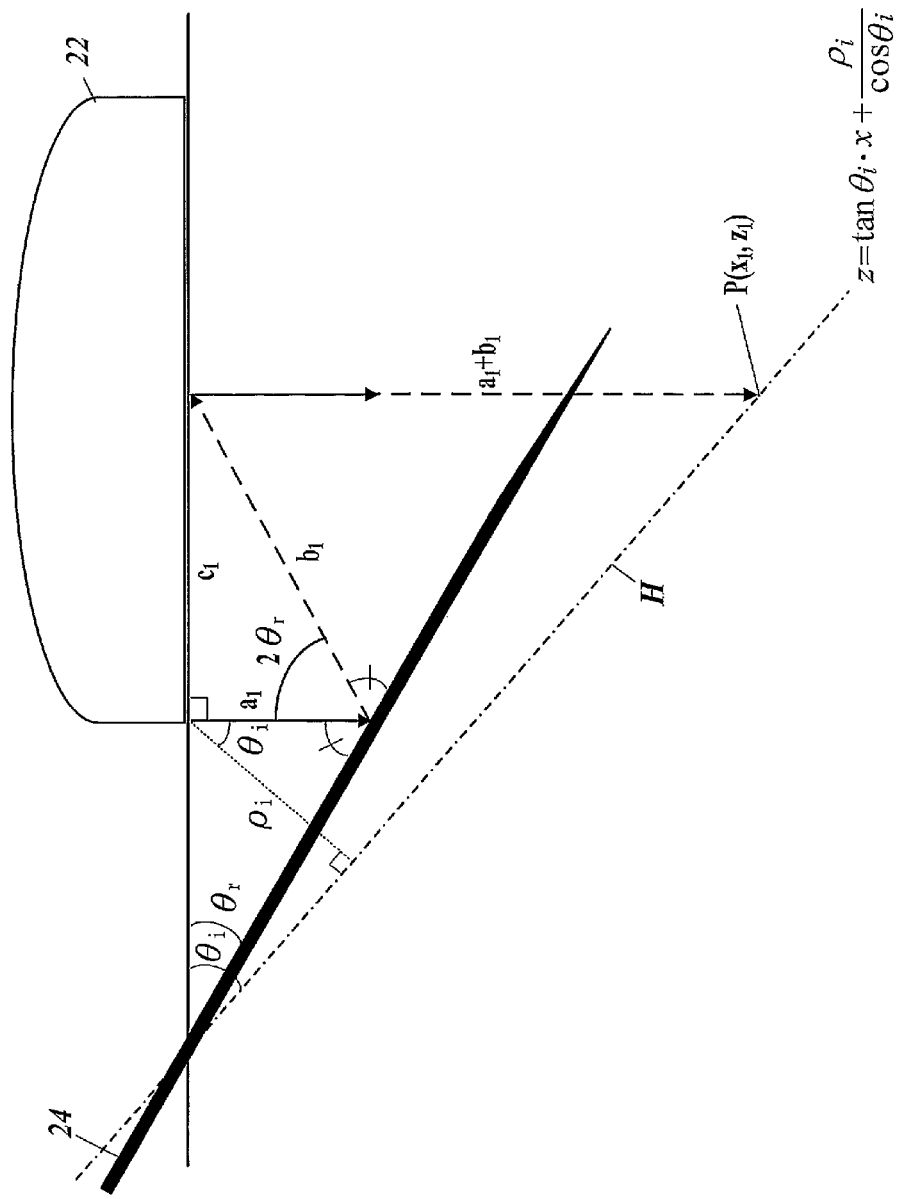
FIG. 15 is a view for describing a method of calculating puncture access information.

With reference to FIG. 15 for example, consider the actual position of the puncture needle 24 by use of a point P $(x_1, y_1)$ on a linear function H of the puncture needle echo information which is based on the received echo data obtained by transmitting the puncture needle searching beam in the direction perpendicular to the orientation direction and receiving it.

The depth $z_1$ of the point P is a sum of a distance $a_1$ from an ultrasound transmission site of the ultrasound probe 22 to the puncture needle 24 and a distance $b_1$ from a reflection point of the ultrasound transmitted from the transmission site on the puncture needle 24 to a receiving site where the reflected ultrasound is received. The depth $z_1$ is accordingly represented by the following formula (6).

$$Z_1 = a_1 + b_1 \quad (6)$$

The ratio of $a_1$ to $b_1$ is represented by the following formula (7).

$$a_1 : b_1 = \cos 2\theta_r : 1 \quad (7)$$

Here, the angle $\theta_r$ represents the actual insertion angle of the puncture needle 24.

Further, $a_1$, $b_1$ and $c_1$ are represented by the following formulae (8) to (10), where $c_1$ represents a distance from the transmission site to receiving site of the ultrasound.

$$a_1 = (z_1 \cdot \cos 2\theta_r)/(1 + \cos 2\theta_r) \quad (8)$$

$$b_1 = z_1/(1 + \cos 2\theta_r) \quad (9)$$

$$c_1 = b_1 \cdot \sin 2\theta_r = (z_1 \cdot \sin 2\theta_r)/(1 + \cos 2\theta_r) \quad (10)$$

Here, $\tan \theta_i$ is determined by the following formula (11) according to the above formula (2) which represents the puncture needle echo information.

$$\tan\theta_i = (a + b) / \{(a / \tan\theta_r) + b\sin 2\theta_r\} \quad (11)$$
$$= \{(1 + \cos 2\theta_r)\tan\theta_r\} / (\cos 2\theta_r + \tan\theta_r \sin 2\theta_r)$$
$$= 2\theta_r$$

Therefore, the actual insertion angle $\theta_r$ of the puncture needle 24 is determined by the following formula (12).

$$\theta_r = \sin^{-1}(\tan\theta_i)/2 \quad (12)$$

Then, when $x_1$ is $c_1$, $z_1$ is determined by the following formula (13).

$$z_1 = \tan\theta_i \cdot x_1 + \rho_i / \cos\theta_i \quad (13)$$
$$= \tan\theta_i \cdot \{z_1 \cdot \sin 2\theta_r / (1 + \cos 2\theta_r)\} + \rho_i / \cos\theta_i$$
$$= \{\rho_i / \cos\theta_i\} \cdot \{(1 + \cos 2\theta_r) / (1 + \cos 2\theta_r - \tan\theta_i \sin 2\theta_r)\}$$

According to the above formulae (8) to (13), the distance $a_1$ from the ultrasound transmission site of the ultrasound probe 22 to the puncture needle 24, i.e. the actual depth Z of the puncture needle 24 is determined by the following formula (14).

$$Z = a_1 \quad (14)$$
$$= (z_1 \cdot \cos 2\theta_r) / (1 + \cos 2\theta_r)$$
$$= \{\rho_i / \cos\theta_i\} \cdot \{\cos 2\theta_r / (1 + \cos 2\theta_r - \tan\theta_i \sin 2\theta_r)\}$$

Figure 16:
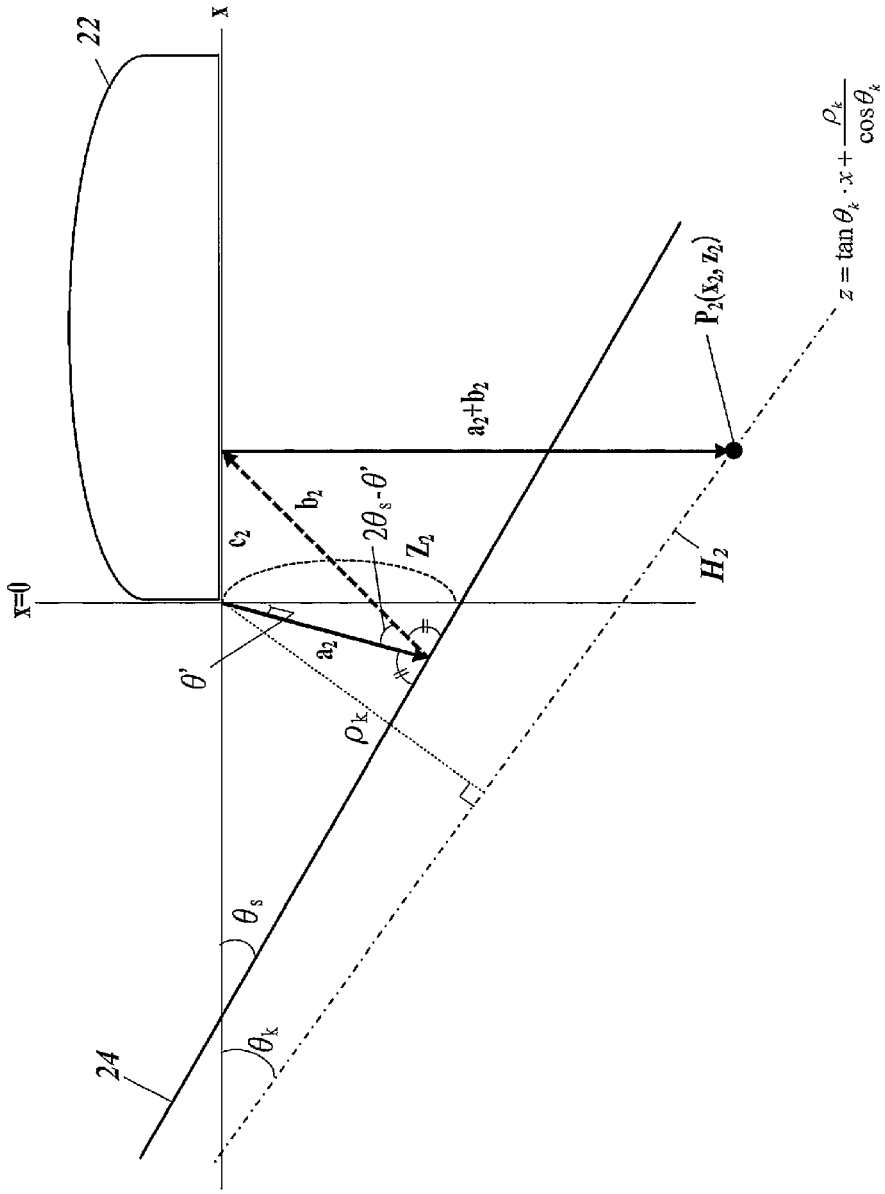
FIG. 16 is a view for describing a method of calculating puncture access information.

Meanwhile, consider the case as shown in FIG. 16 where the puncture access information is obtained based on the receive echo data which is obtained by transmitting the puncture needle searching beam in the direction outward from the ultrasound probe 22 at a predetermined angle $\theta'$ and receiving it. In this case, the puncture needle echo information (z) is represented by the following formula (15).

$$z = \tan\theta_k \cdot x + \rho_k / \cos\theta_k \quad (15)$$

Given a certain point $P_2$ is on a linear function $H_2$ of the punctual needle echo information (z) at a coordinate $(x_2, y_2)$, a depth $z_2$ of the point $P_2$ is a sum of a distance $a_2$ from the ultrasound transmission site of the ultrasound probe 22 to the reflection point on the puncture needle 24 and a distance $b_2$ from the reflection point on the puncture needle 24 to the receiving site where the reflected ultrasound is received as same as the above case. The depth $z_2$ is accordingly represented by the following formula (16).

$$z_2 = a_2 + b_2 \quad (16)$$

The ratio of $a_2$ to $b_2$ is represented by the following formula (17).

$$a_2 : b_2 = \cos(2\theta_s - \theta') : \cos\theta' \quad (17)$$

Further, $a_2$, $b_2$ and $c_2$ are represented by the following formulae (18) to (20), where $c_2$ represents a distance from the transmission site to receiving site of the ultrasound.

$$a_2 = \{z_2 \cdot \cos(2\theta_s - \theta')\} / \{\cos\theta' + \cos(2\theta_s - \theta')\} \quad (18)$$

$$b_2 = (z_2 \cdot \cos\theta') / \{\cos\theta' + \cos(2\theta_s - \theta')\} \quad (19)$$

$$c_2 = b_2 \cdot \sin(2\theta_s - \theta') - a_2 \cdot \sin\theta' = \{z_2 \cdot \sin(2\theta_s - 2\theta')\} / \{\cos\theta' + \cos(2\theta_s - \theta')\} \quad (20)$$

The actual insertion angle $\theta_s$ of the puncture needle 24 is determined by the following formula (21) according to the above formula (15) which represents the puncture needle echo information.

$$\theta_s = \sin^{-1} \tan\theta_k / 2 + \theta'/2 \quad (21)$$

Then, when $x_2$ is $c_2$, $z_2$ is determined by the following formula (22).

$$z_2 = \tan\theta_k \cdot x_2 + \rho_k / \cos\theta_k \quad (22)$$
$$= \tan\theta_k \cdot \{z_2 \cdot \sin(2\theta_s - 2\theta')\} / \{\cos\theta' +$$

-continued
$$\cos(2\theta_s - \theta')\} + \rho_k / \cos\theta_k$$
$$= (\rho_k / \cos\theta_k) \cdot [\{\cos\theta' + \cos(2\theta_s - \theta')\} /$$
$$\{\cos\theta' + \cos(2\theta_s - \theta') - \tan\theta_k \sin(2\theta_s - 2\theta')\}]$$

According to the above formulae (18) to (22), the actual depth $Z_2$ of the puncture needle 24 is determined by the following formula (23).

$$Z_2 = a_2 \cos\theta' + a_2 \sin\theta' \tan\theta_s \quad (23)$$
$$= \{z_2 \cdot \cos(2\theta_s - \theta')(\cos\theta' + \sin\theta' \tan\theta_s)\} /$$
$$\{\cos\theta' + \cos(2\theta_s - \theta')\}$$
$$= (\rho_k / \cos\theta_k) \cdot \{\cos(2\theta_s - \theta')(\cos\theta' + \sin\theta' \tan\theta_s)\} /$$
$$\{\cos\theta' + \cos(2\theta_s - \theta') - \tan\theta_k \sin(2\theta_s - 2\theta')\}$$

As above, the embodiment is successful in generating the puncture access information which specifies the actual insertion angle and depth of the puncture needle 24. The position of the puncture needle 24 is therefore specified more accurately with the obtained received signals.

In the embodiment, the position of the puncture needle 24 is detected by use of the received signals obtained from the puncture needle searching beam. However, if the insertion angle of the puncture needle 24 is shallow enough to obtain the sufficient puncture needle echo information with the scanning beam, the position of the puncture needle 24 may also be detected by applying the Hough transform to the received signals which are obtained by sending and receiving the scanning beam.

When the puncture access information and corrected sound velocity are obtained as described above, the control unit 208 obtains the ultrasound image data for one frame as described below.

Specifically, as shown in FIG. 6, the control unit 208 transmits and receives the scanning beam as described above (step S105).

Next, the control unit 208 sets the delay time of the respective channels for the phasing addition according to the corrected sound velocity as described above (step S106). The phasing addition may not be performed based on the corrected sound velocity, but based on a sound velocity near the corrected sound velocity. The control unit 208 subsequently reads out the received signals from the sampling memory 203c according to the set delay time of the respective channels, and controls the phasing addition unit 203d to co-phase and add them. The control unit 208 thus generates the sound ray data of the biological tissue image data, and outputs it to the image processor 204 (step S107). At this point, the receiving aperture center (the first receiving aperture center) is at the same position with the transmission aperture center of the scanning beam. Here, the ultrasound which is transmitted for displaying a biological tissue is called "the biological tissue image transmission ultrasound". Further, the received signals obtained from the reflected ultrasound output by the ultrasound probe, the reflected ultrasound being the biological tissue image transmission ultrasound reflected off the subject received by the ultrasound probe, are called "the biological tissue image received signals".

Figure 17:
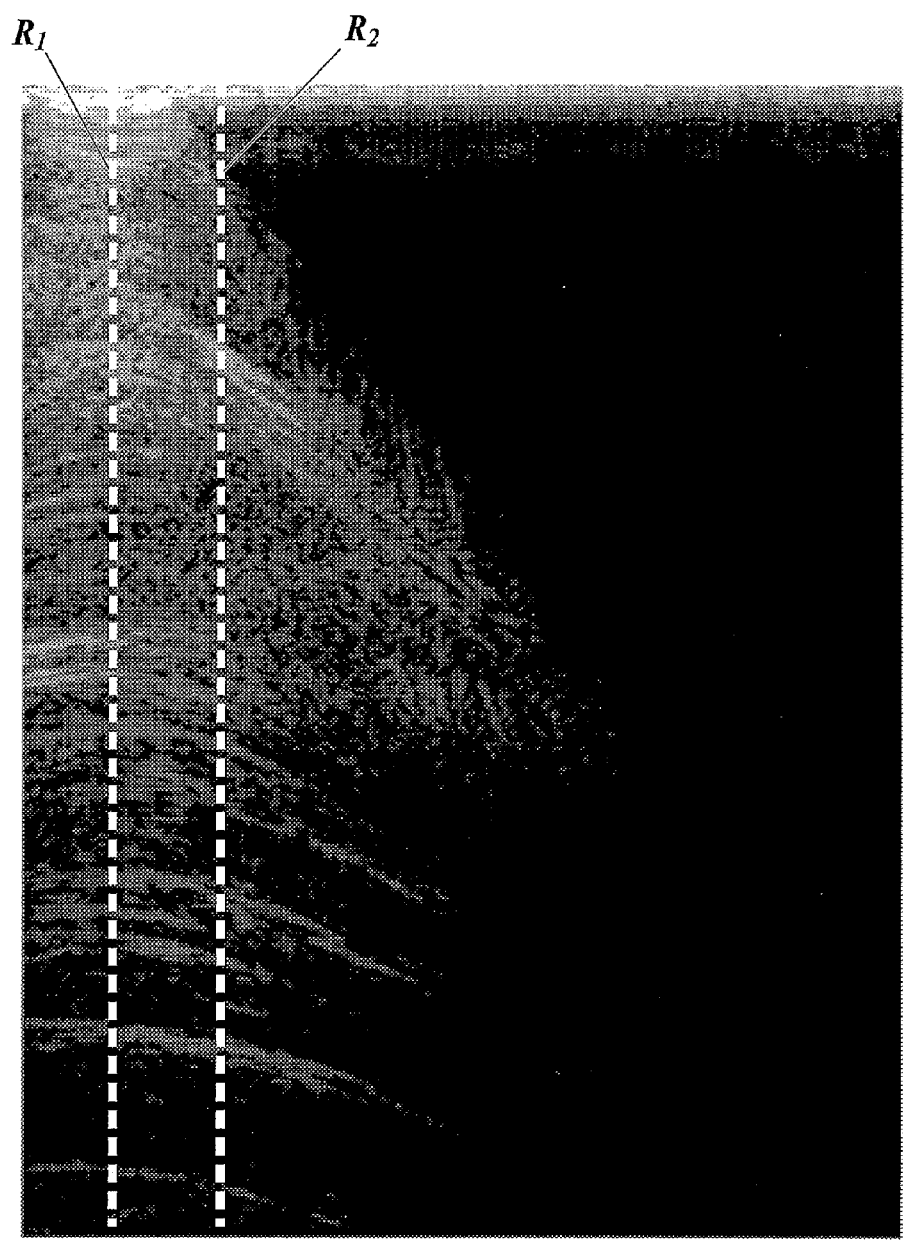
FIG. 17 is a view for describing a receiving aperture center.

Next, the control unit 208 specifies a channel corresponding to the receiving aperture center (the second receiving aperture center) on the basis of the puncture access information according to the transmission aperture center of the scanning beam which is transmitted in step S105 (step S108). That is, the channel corresponding to the second receiving aperture center is specified based on the channel corresponding to the transmission aperture center by application of the puncture access information. As a result, as shown in FIG. 17 for example, the first receiving aperture center, which is set for generating the sound ray data of the biological tissue image data, is located at a position represented by $R_1$ in the figure, while the second receiving aperture center, which is set for generating the sound ray data of the puncture needle image data, is located at a shifted position represented by $R_2$ in the figure. The ultrasound image data which clearly shows the position of the puncture needle 24 are thereby generated.

The control unit 208 reads out the received signals from the sampling memory 203c on the basis of the second receiving aperture center according to the delay time of the respective channels as set above, and controls the phasing addition unit 203d to co-phase and add them. The control unit 208 thus generates the sound ray data of the puncture needle image data, and outputs it to the image processor 204 (step S109).

Figure 18A:
FIGS. 18A, 18B, and 18C are views for describing generation of composite image data according to the embodiment.
Figure 18B:
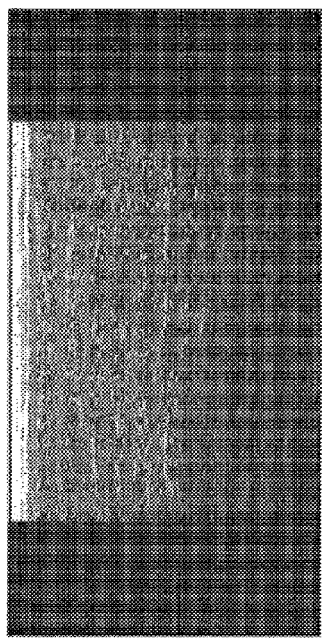
Figure 18C:
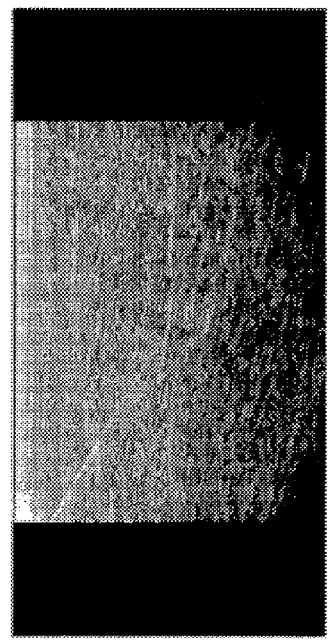

The control unit 208 subsequently determines whether the sound ray data for one frame is obtained or not (step S110). If the control unit 208 determines that the sound ray data for one frame is obtained (step S110, Y), it composites the puncture needle image data which is stored in the puncture needle image frame buffer 205a of the image memory 205 as described above with the biological tissue image data which is stored in the biological tissue image frame buffer 205b so as to generate the composite image data. The control unit 208 stores it to the composite image frame buffer 205c (step S111), and ends the processing. As a result, for example, the biological tissue image data as shown in FIG. 18A and the puncture needle image data as shown in FIG. 18B are composited to be the composite image data shown in FIG. 18C.

Figure 19A:
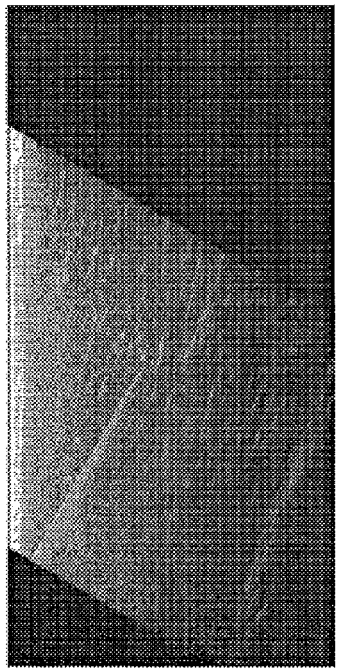
FIGS. 19A, 19B, and 19C are views for describing generation of a composite image data according to the earlier development.
Figure 19B:
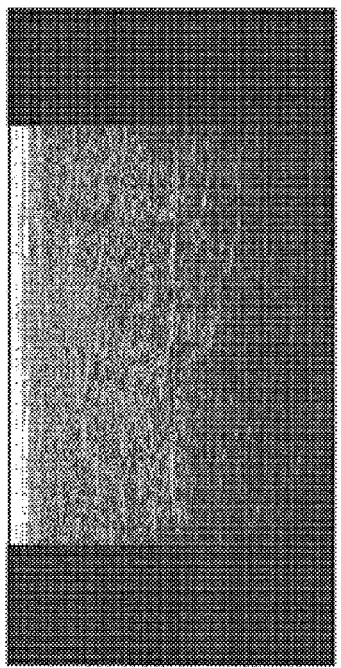
Figure 19C:
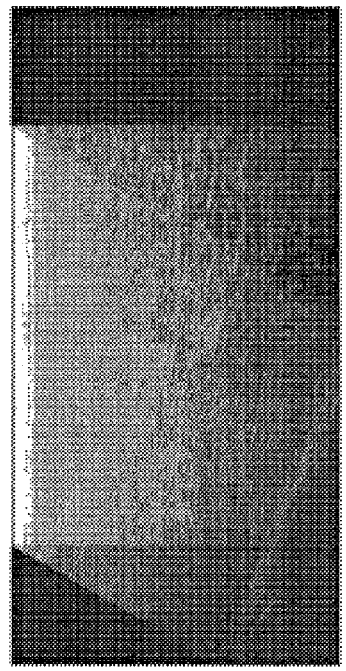

In contrast to the embodiment, the frame rate is inferior in a method of earlier development which performs scanning to obtain a biological tissue image data as shown in FIG. 19A as well as performs scanning with an ultrasound beam directed in the direction toward a puncture needle to obtain a clear puncture needle image data as shown in FIG. 19B. Furthermore, when the biological tissue image data shown in FIG. 19A and the puncture needle image data shown in FIG. 19B are composited, the generated composite image data becomes one as shown in FIG. 19C. Thus, the performance of visualizing the puncture needle is poor.

If the control unit 208 determines in step S110 that the sound ray data for one frame is not obtained (step S110, N), it executes the processing of step S105.

If the control unit 208 determines in step S102 that there is no puncture needle 24 in the subject (step S102, N), it executes a scan processing of normal scanning (step S112) so as to generate the biological tissue image data (step S113), and then ends the processing. That is, if the puncture needle 24 is not detected, it does not generate the puncture needle image data and displays the ultrasound image based on the biological tissue image data.

Figure 9:
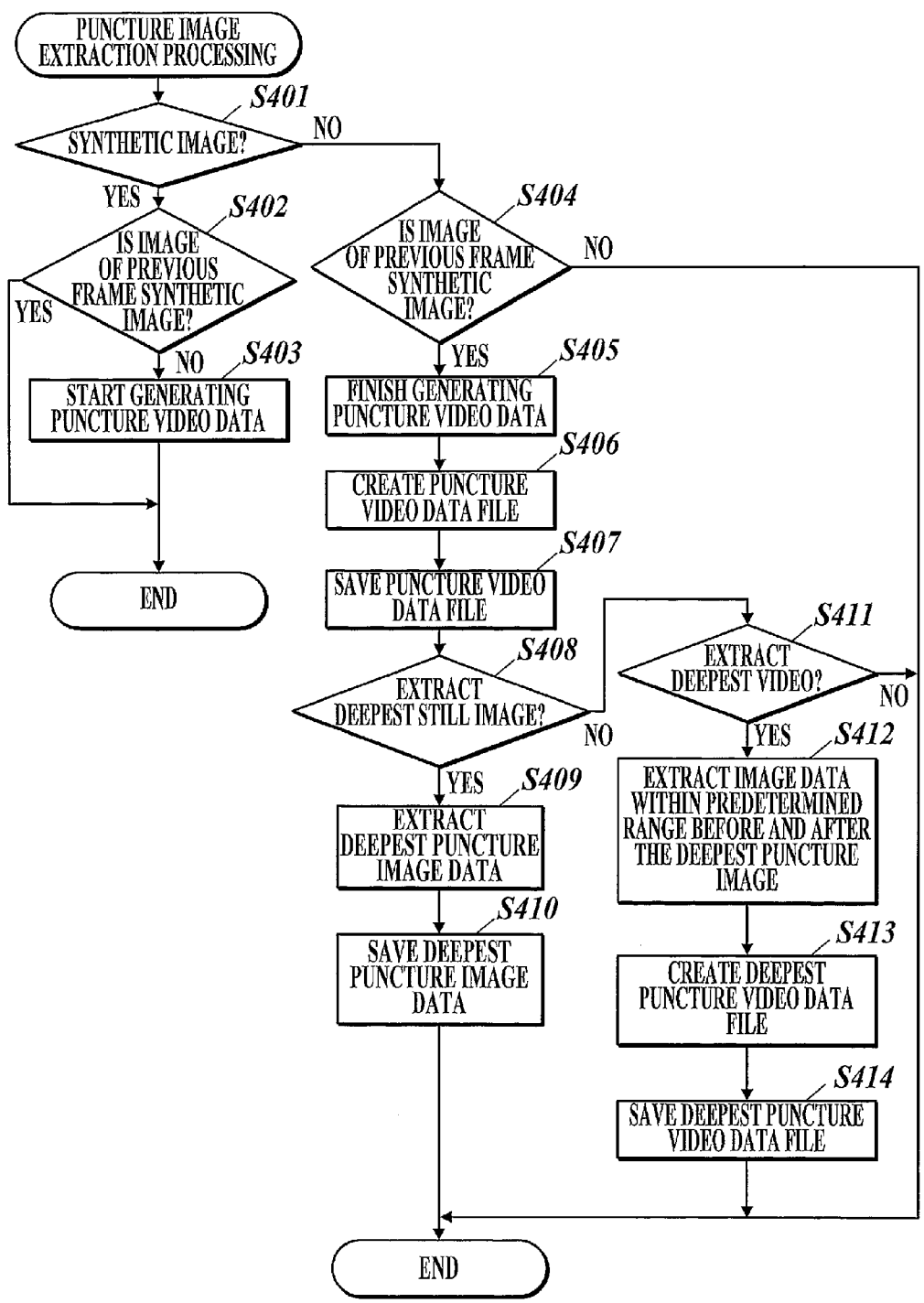
FIG. 9 is a flowchart for describing a puncture image extracting process.

Next, the puncture image extraction processing, which is executed by the control unit 208 of the ultrasound diagnostic imaging apparatus 20, will be described with reference to FIG. 9. The puncture image extraction processing is executed, for example, each time the ultrasound image data for one frame is generated. In the embodiment, the puncture image extraction processing is to extract apart related to the insertion of the puncture needle 24 into the subject from the ultrasound image data as obtained above, and to store it to the storage unit 209 as still image data or video data.

The control unit 208 firstly determines whether the generated ultrasound image data is the above-described composite image data or not (step S401). If the control unit 208 determines that the generated ultrasound image data is the composite image data (step S401, Y), it recognizes that the puncture needle 24 is inserted in the subject, and executes the processing of step S402. The control unit 208 determines in step S402 whether the ultrasound image data on the previous frame is the composite image data or not (step S402). In other words, the control unit 208 determines whether the puncture needle 24 is still inserted in the subject or not. If the control unit 208 determines that the ultrasound image data of the previous frame is not the composite image data (step S402, N), it recognizes that the puncture needle 24 has begun being inserted into the subject. The control unit 208 then starts to generate the puncture video data (step S403), and ends the processing. On the contrary, if the control unit 208 determines that the ultrasound image data of the previous frame is the composite image data (step S402, Y), it recognizes that the puncture video data is being generated. The control unit 208 then ends the processing without executing step S403.

If the control unit 208 determines in step S401 that the generated ultrasound image data is not the composite image data (step S401, N), it recognizes that the puncture needle 24 is not inserted in the subject, and executes the processing of step S404. The control unit 208 determines in step S404 whether the ultrasound image data on the previous frame is the composite image data or not (step S404). If the control unit 208 determines that the ultrasound image data on the previous frame is not the composite image data (step S404, N), it ends the processing without executing the following processing. On the contrary, if the control unit 208 determines that the ultrasound image data on the previous frame was the composite image data (step S404, Y), it recognizes that the puncture needle 24 has been pulled out from the subject, and finishes generating the puncture video data (step S405).

Next, the control unit 208 creates the puncture video data which enables to reproduce multiple frames of the composite image data obtained between the beginning and end of generating the puncture video data in the form of video where they are displayed one after another in chronological order (step S406). The puncture video data file is generated in a predetermined compression format. For example, AVI (audio-video interleaved format), MPEG2 (moving picture experts group 2) and the like are applicable.

The control unit 208 saves the puncture video data file as created above to the storage unit 209 (step S407).

Next, the control unit 208 determines whether it extracts a still image which shows the puncture needle 24 at the deepest position from the composite image data included in the puncture video data file or not (step S408). Whether extracting the still image which shows the puncture needle 24 at the deepest position or not is determined based on, for example, whether a predetermined operation is made by the operation input unit 201 or not. If the control unit 208 determines that it extracts the still image which shows the puncture needle 24 at the deepest position (step S408, Y), it extracts the still image which shows the puncture needle 24 at the deepest position from the composite image data included in the puncture video data file (step S409). Specifically, the control unit 208 reads out, for example, each puncture needle image data which correspond to the composite image data included in the puncture video data file. The control unit 208 reads them out from the puncture needle image frame buffer 205a, and quantizes them into respective binary data. The control unit 208 develops each binarized puncture needle image data onto an x-y space. The control unit 208 determines a distance from the insert position to the tip position of the puncture needle 24 with respect to each puncture needle image data developed on the x-y space, and compares them. Regarding the target of the comparison, the integrals about the x-axis may be compared to specify the deepest puncture needle image data. Further, the lengths of the puncture needle may be determined by means of trigonometric function and compared. Alternatively, the composite image data which shows the puncture needle 24 at the deepest position may be extracted by holding the results of the Hough transform on the received echo data as generated above with respect to each frame and extracting the composite image data which corresponds to the frame having the maximum votes. In the embodiment, the composite data which shows the puncture needle 24 at the deepest position is extracted from the composite image data obtained between the beginning and end of generating the puncture video data. However, every time the ultrasound image data is generated, it may be held as the composite data which shows the puncture needle 24 at the deepest position if the depth of the puncture needle 24 is deeper than those of previously obtained composite image data. The composite image data which is held at the end may be then saved as the still image which shows the puncture needle 24 at the deepest position.

The control unit 208 stores the composite image data as extracted above in the storage unit 209 (step S410), and ends the processing.

If the control unit 208 determines in step S408 that it does not extract the still image which shows the puncture needle 24 at the deepest position (step S408, N), it determines whether it extracts the composite image data to generate the video data or not, in which the composite image data are multiple frames of data consisting of the composite image data which shows the puncture needle 24 at the deepest position and other composite image data within a predetermined time period before and after it and the video data is data which displays these data one after another in chronological order (step S411). Based on whether a predetermined operation is made on the operation input unit 201 or not, for example, the control unit 208 determines whether it extracts the composite image data to generate the video data or not, in which the composite image data are multiple frames of data consisting of the composite image data which shows the puncture needle 24 at the deepest position and other composite image data within the predetermined time period before and after it and the video data is data which displays these data one after another in chronological order The time period of extracting the composite image data may be set appropriately.

If the control unit 208 determines that it extracts the composite image data to generate the video data, in which the composite image data are multiple frames of data consisting of the composite image data which shows the puncture needle 24 at the deepest position and other composite image data within the predetermined time period before and after it and the video data is data which displays these data one after another in chronological order (step S411, Y), it extracts the composite image data which shows the puncture needle 24 at the deepest position, as well as other composite image data within the predetermined time period before and after it (step S412). The control unit 208 then creates the deepest puncture video data file for reproducing these composite image data in the form of video which displays them one after another in chronological order (step S413). The control unit 208 saves the deepest puncture picture motion data file as created above in the storage unit 209 (step S407), and ends the processing.

If the control unit 208 determines in step S411 that it does not extract the composite image data to generate the video data, in which the composite image data are multiple frames of data consisting of the composite image data which shows the puncture needle 24 at the deepest position and other composite image data within the predetermined time period before and after it and the video data is data which displays these data one after another in chronological order (step S411, N), it ends the processing without executing the processing of steps S412 to S414.

The deepest puncture image data and deepest puncture video data as generated above are converted to image files according to the DICOM standard, and sent to the PACS 30 and the like. At this point, ultrasound image data which are obtained between the beginning and end of the ultrasound diagnostic imaging may be also converted to image files and sent to the PACS 30 and the like as well as the deepest puncture image data and deepest puncture video data.

Since the deepest puncture image data and deepest puncture video data are generated as described above, the embodiment is successful in storing them as medical records as well as holding them as suitable images for the use of informed consent.

In view of the foregoing, according to the embodiment, the ultrasound probe 22 outputs the transmission ultrasound toward the subject as driven by the driving signal as well as outputs the received signals which are obtained by receiving the reflected ultrasound from the subject. The transmission unit 202 applies the driving signal to the ultrasound probe 22. The receiving unit 203 receives the received signals output from the ultrasound probe 22. The transmission unit 202 applies the driving signal to the ultrasound probe 22 in such a way that the ultrasound probe 22 outputs the plane-wave transmission ultrasound. The receiving unit 203 receives the plane-wave received signals from the ultrasound probe 22 which is obtained in such a way that the ultrasound probe 22 transmits the plane-wave transmission ultrasound, the puncture needle 24 which is inserted in the subject reflects it, and the ultrasound probe 22 receives the reflected ultrasound. Based on the plane-wave received signals received by the receiving unit 203, the puncture needle position detection unit 203e obtains the puncture needle echo information which indicates the angle and position of the puncture needle 24 inserted in the subject. As a result, since the plane-wave ultrasound is sent and received to specify the position of the puncture needle, the decrease in frame rate is reduced in specifying the position of the puncture needle.

According to the embodiment, the puncture needle position detection unit 203e performs the Hough transform on the plane-wave received signals received by the receiving unit 203, and obtains the puncture needle echo information based on the results of the Hough transform. As a result, the position of the puncture needle is specified with high accuracy. Even if the received signals are interrupted in the middle, the position of the puncture needle is specified well.

According to the embodiment, the puncture needle position detection unit 203e extracts the edge on the basis of change in intensity of the plane-wave received signals received by the receiving unit 203. The puncture needle detector 203e performs the Hough transform on the edge-extracted plane-wave received signals. As a result the position of the puncture needle is specified with higher accuracy.

According to the embodiment, the puncture needle position detection unit 203e develops each of the plane-wave received signals which are received from the respective multiple transducers 22a by the receiving unit 203, onto an x-y space where x and y axes represent the position of each transducer 22a and the depth respectively. The puncture needle position detection unit 203e performs the Hough transform on the received signals developed on the x-y space.

The puncture needle position detection unit 203e obtains a plurality of sine curves as the results of the Hough transform, specifies the straight line on the x-y space based on the point which wins the largest number of votes, which represents the number of the sine curves through a certain point, and obtains the puncture needle echo information based on the straight line. As a result, the position of the puncture needle is easily specified with high accuracy.

According to the embodiment, the puncture needle position detection unit 203e detects the edge intensity on the basis of change in intensity of the plane-wave received signals received by the receiving unit 203. The puncture needle position detection unit 203e weights the votes with respect to each of the sine curves according to the detected edge intensity. As a result, the position of the puncture needle is specified with higher accuracy.

According to the embodiment, the puncture needle position detection unit 203e obtains the puncture access information on the basis of the distance between the ultrasound probe 22 and the straight line which is determined by the obtained puncture needle echo information. The puncture access information indicates the insertion angle and depth of the puncture needle 24 inserted in the subject. As a result, the position of the puncture needle is specified with higher accuracy.

According to the embodiment, the phasing addition unit 203d co-phases and adds the received signals obtained from the reflected ultrasound from the subject with reference to the first receiving aperture center. The control unit 208 generates the image data for displaying the ultrasound image on the basis of the co-phased and added received signals. The phasing addition unit 203d sets a shift amount which is applied to the receiving aperture center on the basis of the puncture access information. The phasing addition unit 203d performs the phasing addition with reference to the second receiving aperture center, which is shifted from the first receiving aperture center by the set shift amount. Based on the received signals which are co-phased and added by the phasing addition unit 203d with reference to the second receiving aperture center, the control unit 208 generates the puncture needle image data in which the part of the puncture needle image, which is the image of the puncture needle 24 inserted in the subject, is enhanced. As a result, the position of the puncture needle is visualized with high accuracy, and the ultrasound image data which clearly shows the position of the puncture needle is thus generated.

According to the embodiment, the control unit 208 composites the puncture needle image data and the biological tissue image data generated from the received signals which are co-phased and added with reference to the first receiving aperture center. As a result, the puncture needle image is clearly shown on the biological tissue image.

Figure 20A:
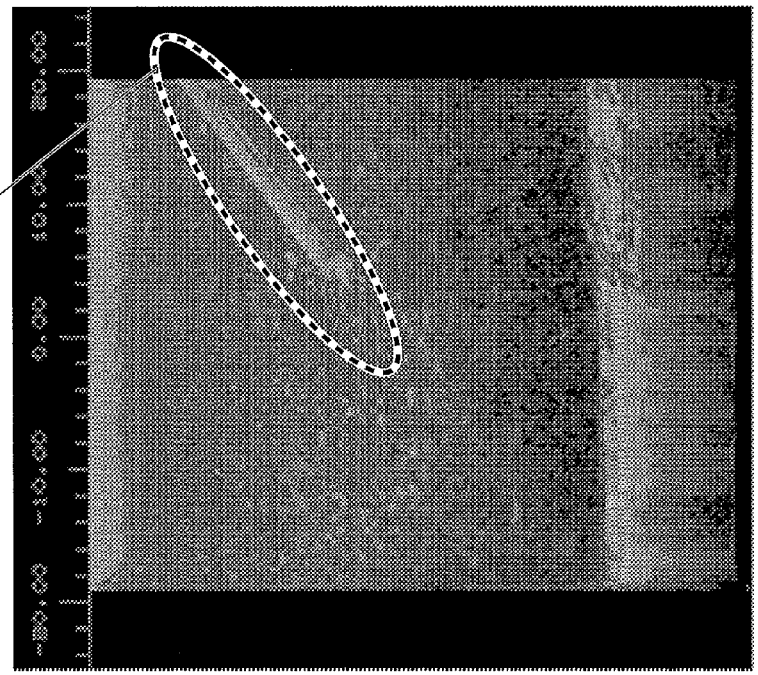
FIG. 20A is a view for describing an advantageous effect of the embodiment.
Figure 20B:
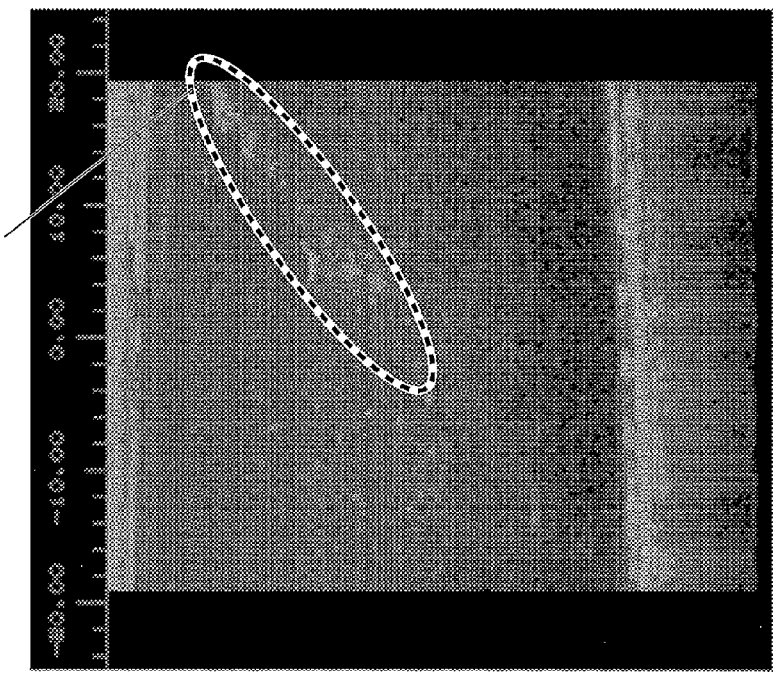
FIG. 20B is a view for describing an advantageous effect of an embodiment.

For example, if the puncture needle image data is not generated and the puncture needle is specified only with the biological tissue image data, the puncture needle does not show up clearly as seen in the area S1 surrounded by the dotted line in FIG. 20A. It is thus difficult to manipulate the puncture needle as visually recognizing it in the ultrasound image. In contrast, according to the embodiment, the puncture needle shows up clearly as seen in the area S2 surrounded by the dotted line in FIG. 20B. The puncture needle can be therefore manipulated accurately as visually recognizing it in the ultrasound image.

Here, the image processor 204 performing logarithmic compression on the sound ray data and then adjusts the dynamic range and gain so as to convert signals of the sound ray data to brightness. However, the ultrasound image data may be generated as follows.

Figure 21:
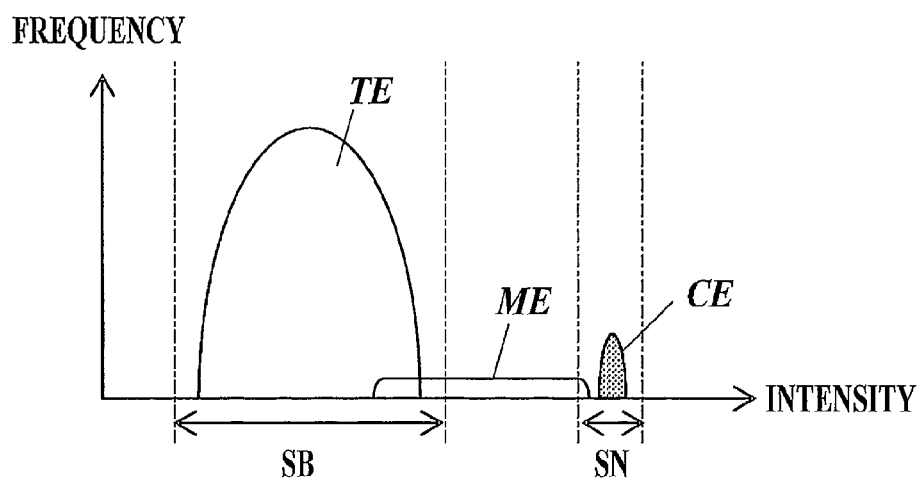
FIG. 21 is a view for describing a histogram of the received signal.

For example, FIG. 21 shows the received signals for one frame as generated above shown in the form of a histogram. The received signals CE which are obtained from the reflected ultrasound from the metal puncture needle has stronger signal intensity than the received signals TE which are obtained from the reflected ultrasound from the subject tissue. The intensity range SN of the received signals which are obtained from the reflected ultrasound from the puncture needle is narrower than the intensity range SB of the received signals which are obtained from the reflected ultrasound from the subject tissue.

Figure 22C:
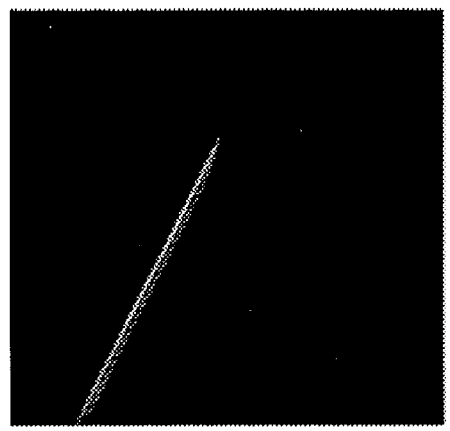
FIG. 22C is a view for describing reduction in multiple reflection.
Figure 22B:
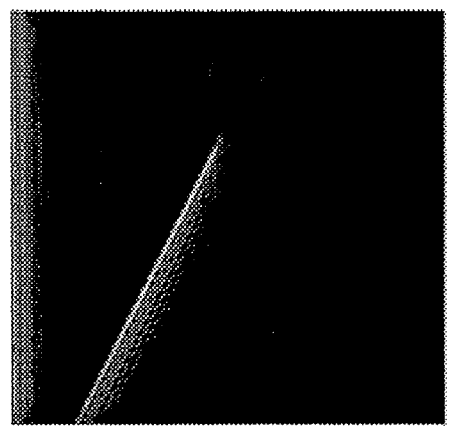
FIG. 22B is a view for describing reduction in multiple reflection.
Figure 22A:
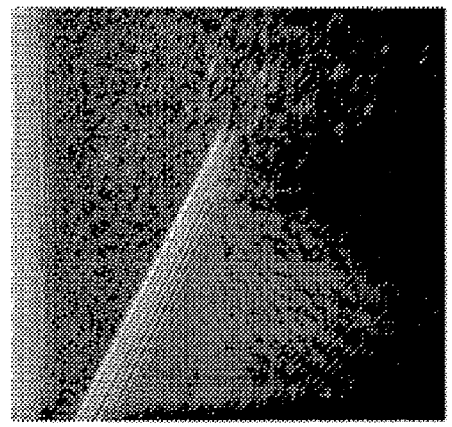
FIG. 22A is a view for describing reduction in multiple reflection.

If the sound ray data of the puncture needle image data is processed by logarithmic compression as performed in the earlier development, multiple reflection occurs on the high-reflector puncture needle. The sound ray data thus includes a received signal ME caused by multiple echo as shown in FIG. 21. As a result, other signal components besides the puncture needle may show up to be artifacts as shown in FIG. 22A.

To cope with this, in the embodiment, the image processor 204 may be controlled to reduce low-intensity signal components in such a way that only the sound ray data of the biological tissue image data is log-compressed and the sound ray data of the puncture needle image data is not log-compressed, and performing setting in dynamic range and the like so as to extract signals having a signal intensity within a predetermined range which covers the signal intensity of the received signals obtained from the ultrasound beam reflected on the puncture needle. In replace of or in addition to the dynamic range setting, for example, a LUT (look up table) which linearly converts received signal intensity to brightness may be used. As a result, it is achieved to obtain the puncture needle image data in which artifacts caused by the multiple reflection is reduced as shown in FIG. 22B.

As above, according to the embodiment, the processor 204 converts intensity of the received signals which are co-phased and added by phasing addition unit 203$d$ to brightness so as to generate image data. The image processor 204 log-compresses the received signals which are co-phased and added with reference to the first receiving aperture center so as to generate image data and it extracts the received signals in a predetermined intensity range from the receives signals which are co-phased and added with reference to the second receiving aperture center and converts intensity of the extracted signals to brightness so as to generate the puncture needle image data.

In the embodiment, the insertion angle and depth of the puncture needle are determined by the puncture access information. Based on them, the image processor 204 may apply masking so that the conversion to brightness is only applied to an area corresponding to the position of the puncture needle. As a result, as show in FIG. 22C, it is achieved to obtain the puncture image data in which the artifacts caused by the multiple reflection are further reduced as well as the image data based on the received signals of the reflected ultrasound from the subject tissue. The masking may be applied either before converting the signal intensity of the received signals to brightness or after converting the signal intensity of the received signals to brightness.

As above, according to the embodiment, the image processor 204 sets the area for generating the puncture needle data on the basis of the puncture access information. The image processor 204 generates the puncture image data of the sets region on the basis of the received signals which are co-phased and added with reference to the second receiving aperture center.

According to the embodiment, the sound velocity calculation unit 203$f$ calculates the sound velocity in the subject on the basis of the puncture needle echo information which is obtained by the puncture needle position detection unit 203$e$. As a result, the medium of the subject is specified, for example.

According to the embodiment, the phasing addition unit 203$d$ co-phases and adds the received signals on the basis of the sound velocity calculated by the sound velocity calculation unit 203$f$. As a result, the phase addition is performed correctly according to the medium of the subject, and the ultrasound image is thus obtained with high definition.

Figure 23B:
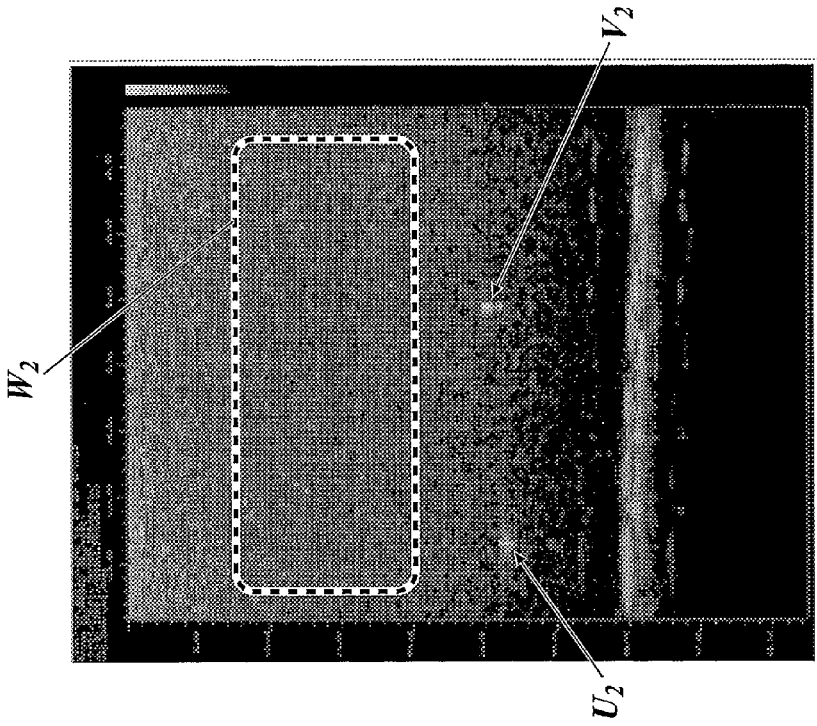
FIG. 23B is a view for describing an advantageous effect of an embodiment.
Figure 23A:
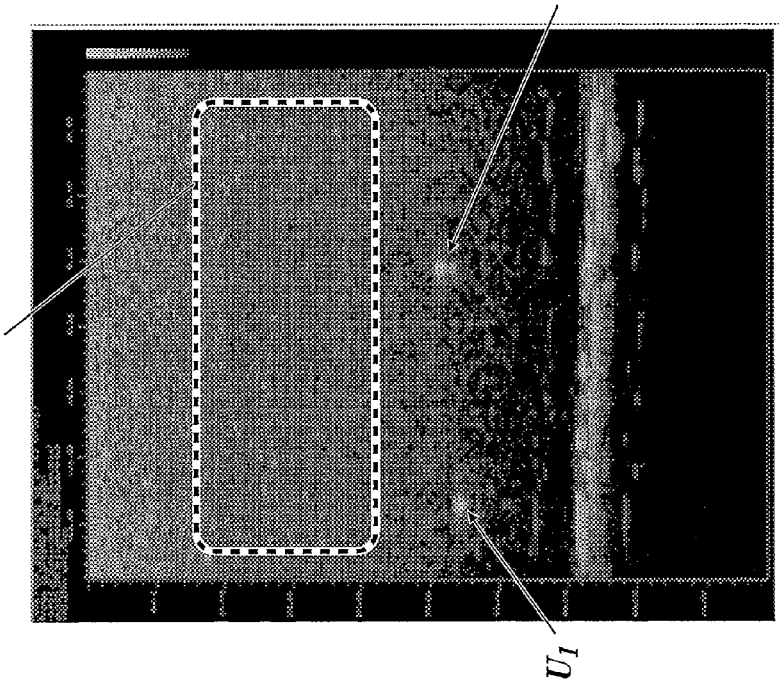
FIG. 23A is a view for describing an advantageous effect of an embodiment.
Figure 24A:
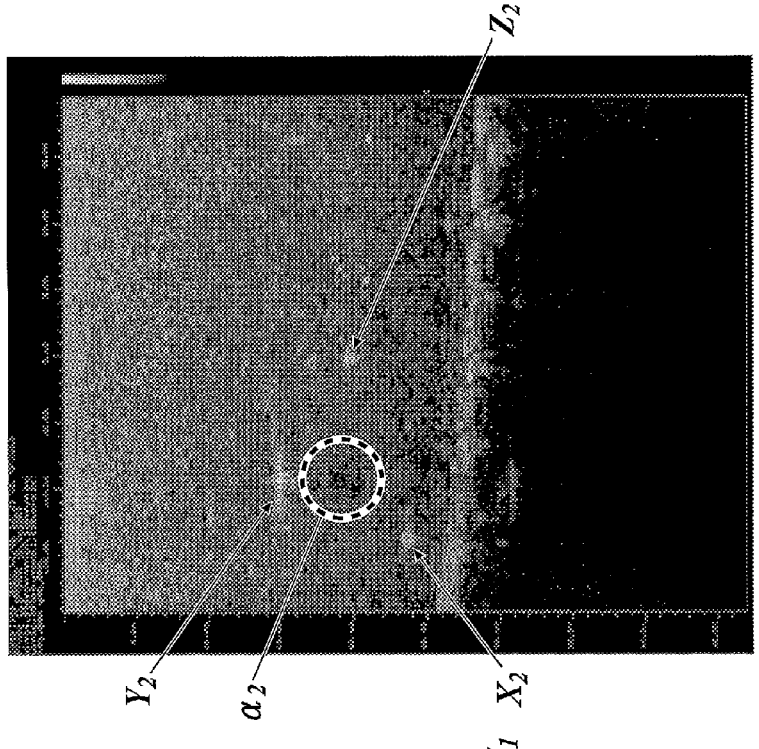
FIG. 24A is a view for describing an advantageous effect of an embodiment.
Figure 24B:
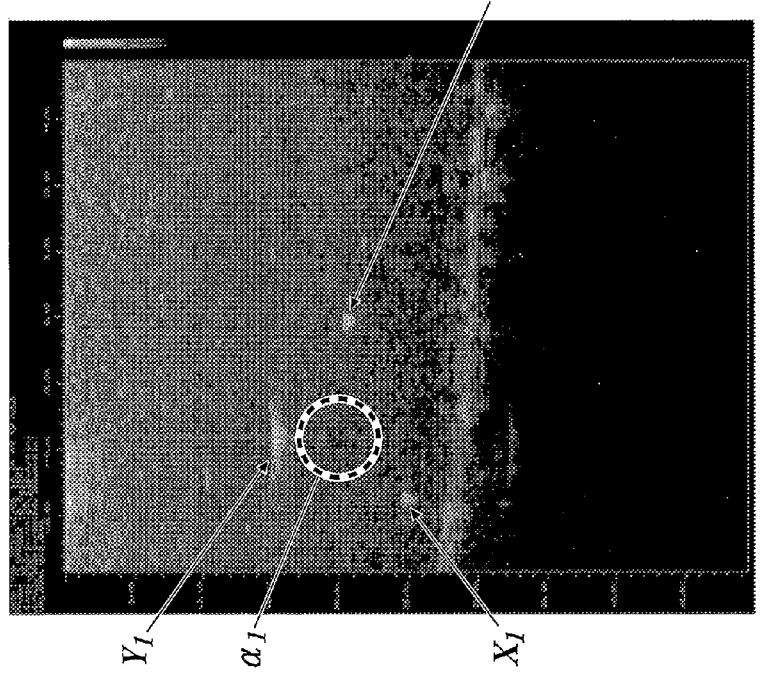
FIG. 24B is a view for describing an advantageous effect of an embodiment.

For example, if the phase addition is performed on the basis of a tentative sound velocity (e.g. 1,540 m/s) which is different from the actual sound velocity (e.g. 1,472 m/s) in the medium of the subject, the orientation resolution is low at the reflectors $U_1$, $V_1$, $X_1$, $Y_1$ and $Z_1$ in the subject as shown in FIGS. 23A and 24A. Also, the graininess of speckles is poor as shown in the area $W_1$ in FIG. 23A. Further, there is much noise in a so-called anechoic area as shown in the area $\alpha_1$ in FIG. 24A, and the obtained ultrasound image thus has poor clearness. In contrast, if the phase addition is performed based on the sound velocity in the medium of the subject or one close to it (e.g. 1,475 m/s), the orientation resolution is improved at the reflectors $U_2$, $V_2$, $X_2$, $Y_2$ and $Z_2$ in the subject as shown in FIGS. 23B and 24B. Also, the graininess of speckles is improved as shown in the area $W_2$ in FIG. 23A. Further, the noise in a so-called anechoic area is suppressed as shown in the area $\alpha_2$ in FIG. 24B.

According to the embodiment, the transmission unit 202 applies the driving signal to the ultrasound probe in such a manner that the plane-wave transmission ultrasound is output from an end of the ultrasound probe 22. As a result, the puncture needle is rapidly detected.

According to the embodiment, the transmission unit 202 applies the driving signal to the ultrasound probe 22 in such a manner that the plane-wave transmission ultrasound is output from both orientation ends of the ultrasound probe 22. As a result, the puncture needle is rapidly detected regardless of which side of the ultrasound probe it is inserted into the subject from.

According to the embodiment, the transmission unit 202 applies the driving signal to the ultrasound probe 22 in such a manner that the plane-wave transmission ultrasound is output from the ultrasound probe 22 in the direction outward from the ultrasound probe 22 at a predetermined angle to the depth direction. As a result, the ultrasound probe receives the plane-wave transmission ultrasound reflected from the puncture needle in large amount, and the position of the puncture needle is thus specified with higher accuracy.

The description of the embodiment of the present invention is an example of the ultrasound diagnostic imaging apparatus according to the present invention and the present invention is not limited thereto. Detail configuration and detail operation of each functional unit constituting the ultrasound diagnostic imaging apparatus can also be modified arbitrarily.

In the embodiment, the ultrasound diagnostic imaging apparatus is established on the medical image management system, however the ultrasound diagnostic imaging apparatus may not be connected to a network.

In the embodiment, the Hough transform is employed in order to obtain the puncture needle echo information, however other methods may be employed to obtain the puncture needle echo information. For example, such methods as template matching and brightness analysis may be employed to obtain the puncture needle echo information.

In the embodiment, the edge detection is performed on the received echo data prior to the Hough transform, however the Hough transform may be performed on the received echo data without the edge detection.

In the embodiment, the method for obtaining the puncture access information is not limited to the above-described method, and any method may be employed as long as the actual insert angle and depth of the puncture needle in the subject can be specified.

In the embodiment, the puncture needle image data is generated on the basis of the receive echo data, and this puncture needle image data is composited with the biological tissue image data to generate the composite image data. However, the puncture needle image data based on the received data may not be generated. For example, a puncture needle image may be virtually drawn based on the puncture needle echo information and puncture needle access information, and it may be composited with the biological tissue image data. Furthermore, a guide display to guide the insertion of the puncture needle may be displayed on the basis of the puncture needle echo information and puncture needle access information.

In the embodiment, the sound velocity is corrected, and the phase addition is performed based on the corrected sound velocity. However, the sound velocity may not be corrected.

In the embodiment, the puncture needle echo information and puncture access information are obtained and the sound velocity is corrected in each frame. However they may be performed in units of multiple frames.

In the embodiment, the puncture video data file, deepest puncture image data and deepest puncture video data file are generated from the obtained composite image data. However, only a part of them may be generated. Also, they may not be generated.

In the embodiment, the deepest puncture image data is extracted from the obtained composite image data. However, a composite image data in which the puncture needle is not at the deepest position may be extracted and saved.

In the embodiment, the image data of the puncture needle inserted in the subject is extracted from the obtained ultrasound image data, the image data file is generated from the extracted image data and is sent to an external device such as PACS on the network. However, the image data file may not be sent to an external device on the network.

In the embodiment, use of a hard disk or non-volatile semiconductor memory is disclosed as examples of a computer-readable medium for the programs of the invention. However, it is not limited to these examples. A portable recoding medium such as CD-ROM is another example of the computer-readable medium which can be employed. A carrier wave may also be employed as a medium which enables to provide the program data of the invention through communication lines.

The entire disclosure of Japanese Patent Application No. 2012-060594 filed on Mar. 16, 2012 is incorporated herein by reference in its entirety.

What is claimed is:

1. An ultrasound diagnostic imaging apparatus, comprising:
   an ultrasound probe which is driven by a driving signal to output a transmission ultrasound toward a subject and which outputs a received signal obtained by receiving a reflected ultrasound from the subject;
   a transmission circuit which applies, as the driving signal, a first driving signal to the ultrasound probe so that a puncture needle searching transmission ultrasound is output from the ultrasound probe as the transmission ultrasound, the puncture needle searching transmission ultrasound being a plane-wave;
   a receiving circuit which receives a puncture needle searching received signal output from the ultrasound probe as the received signal, the puncture needle searching received signal being obtained from the reflected ultrasound which is the puncture needle searching transmission ultrasound reflecting off the subject being received by the ultrasound probe; and
   a processor which performs control to obtain puncture needle echo information indicating an angle and a position of a puncture needle inserted in the subject from the puncture needle searching received signal received by the receiving circuit,
   wherein:
   the transmission circuit applies, as the driving signal, a second driving signal to the ultrasound probe so that a scanning beam which is an ultrasound beam to be focused is output from the ultrasound probe as the transmission ultrasound, and
   the processor performs control to add delay time to a plurality of received signals obtained by receiving the reflected ultrasound of the scanning beam from the subject and to add up the received signals to generate sound ray data, wherein the sound ray data is generated based on the puncture needle echo information.

2. The ultrasound diagnostic imaging apparatus of claim 1, wherein the processor performs a Hough transform on the puncture needle searching received signal received by the receiving circuit, and obtains the puncture needle echo information based on a result of the Hough transform.

3. The ultrasound diagnostic imaging apparatus of claim 2, wherein the processor extracts an edge based on change in intensity of the puncture needle searching received signal received by the receiving circuit, and performs the Hough transform on the puncture needle searching received signal in which the edge is detected.

4. The ultrasound diagnostic imaging apparatus of claim 2, wherein:
   the ultrasound probe comprises a plurality of transducers and outputs the transmission ultrasound from the plurality of transducers, and
   the processor develops the puncture needle searching received signal of each of the plurality of the transducers received by the receiving circuit onto an x-y space where x and y represent a position of each transducer and a depth respectively, performs the Hough transform on the puncture needle searching received signal developed on the x-y space, and obtains the puncture needle echo information based on a straight line on the x-y space which is specified by a point having a maximum vote, the vote being a number of sine curves which pass through the point among a plurality of sine curves obtained by the Hough transform.

5. The ultrasound diagnostic imaging apparatus of claim 4, wherein the processor detects an edge intensity based on change in intensity of the puncture needle searching received signal received by the receiving circuit, and weights the vote with respect to each of the plurality of the sine curves according to the detected edge intensity.

6. The ultrasound diagnostic imaging apparatus of claim 1, wherein the processor obtains puncture access information which specifies the angle and the depth of the puncture needle inserted in the subject based on a distance between the ultrasound probe and a straight line which is determined by the obtained puncture needle echo information.

7. The ultrasound diagnostic imaging apparatus of claim 6, wherein the processor performs control to:
co-phase and add, with reference to a first receiving aperture center, the plurality of received signals obtained by receiving the reflected ultrasound of the scanning beam, wherein the plurality of received signals which are co-phased and added with respect to the first receiving aperture center are biological tissue image transmission received signals,
generate biological tissue image data from the biological tissue image transmission received signals which are co-phased and added with reference to the first receiving aperture center,
set a shift amount of a second receiving aperture center based on the puncture access information, and co-phase and add, with reference to the second receiving aperture center, the plurality of received signals obtained by receiving the reflected ultrasound of the scanning beam to thereby generate the sound ray data, wherein the second receiving aperture center is shifted by the set shift amount from the first receiving aperture center, and
generate puncture needle image data in which a puncture needle image is enhanced based on the sound ray data which is generated by co-phasing and adding the plurality of received signals with reference to the second receiving aperture center, the puncture needle image being an image of the puncture needle inserted in the subject.

8. The ultrasound diagnostic imaging apparatus of claim 7, wherein the processor composites the puncture needle image data with the biological tissue image data generated from the biological tissue image received signals which are co-phased and added with reference to the first receiving aperture center.

9. The ultrasound diagnostic imaging apparatus of claim 8, wherein the processor performs control to:
generate the biological tissue image data by log-compressing the biological tissue image received signals which are co-phased and added with reference to the first receiving aperture center and converting intensity of the biological tissue image received signals to brightness, and
generate the puncture needle image data by extracting a received signal having a predetermined intensity among the plurality of received signals which are co-phased and added with respect to the second receiving aperture center, and converting the intensity of the extracted received signal to brightness.

10. The ultrasound diagnostic imaging apparatus of claim 8, wherein the processor defines an area from which the puncture needle image data is generated based on the puncture access information, and performs control to generate the puncture needle image data of the defined area from the plurality of received signals which are co-phased and added with reference to the second receiving aperture center.

11. The ultrasound diagnostic imaging apparatus of claim 7, wherein the processor performs control to calculate a sound velocity in the subject based on the obtained puncture needle echo information.

12. The ultrasound diagnostic imaging apparatus of claim 11, wherein the processor performs control to co-phase and add the plurality of received signals with reference to the first receiving aperture center and the second receiving aperture center, respectively, based on the calculated sound velocity.

13. The ultrasound diagnostic imaging apparatus of claim 1, wherein:
the ultrasound probe includes a plurality of transducers which are arranged in a first direction and which output the puncture needle searching transmission ultrasound, and
the transmission circuit applies the first driving signal to the ultrasound probe so that the puncture needle searching transmission ultrasound is output from an end of the transducers in the first direction.

14. The ultrasound diagnostic imaging apparatus of claim 13, wherein the transmission circuit applies the first driving signal to the ultrasound probe so that the puncture needle searching transmission ultrasound is output from both ends of the transducers in the first direction.

15. The ultrasound diagnostic imaging apparatus of claim 1, wherein:
the ultrasound probe includes a plurality of transducers which are arranged in a first direction and which output the puncture needle searching transmission ultrasound, and
the transmission circuit applies the first driving signal to the ultrasound probe so that the transducers output the puncture needle searching transmission ultrasound in a direction outward from the transducers in the first direction at a certain angle to a depth direction.

16. The ultrasound diagnostic imaging apparatus of claim 1, wherein
the sound ray data generated based on the received signals obtained from the reflected ultrasound of the scanning beam from the subject and the puncture needle echo information is sound ray data of puncture needle image data, and
the processor performs control to:
generate sound ray data of biological tissue image data based on the received signals obtained from the reflected ultrasound of the scanning beam from the subject,
generate biological tissue image data based on the sound ray data of biological tissue image data, and generate puncture needle image data based on the sound ray data of puncture needle image data; and
composite the puncture needle image data with the biological tissue image data.

* * * * *